United States Patent
Maekawa et al.

(10) Patent No.: US 10,988,579 B2
(45) Date of Patent: *Apr. 27, 2021

(54) ORGANOPOLYSILOXANE GRAFT POLYMER

(71) Applicant: KAO CORPORATION, Tokyo (JP)

(72) Inventors: Tomoka Maekawa, Wakayama (JP);
Shuichiro Kobaru, Tokyo (JP);
Chihiro Miyazaki, Wakayama (JP)

(73) Assignee: KAO CORPORATION, Tokyo (JP)

(*) Notice: Subject to any disclaimer, the term of this patent is extended or adjusted under 35 U.S.C. 154(b) by 260 days.

This patent is subject to a terminal disclaimer.

(21) Appl. No.: 15/895,717

(22) Filed: Feb. 13, 2018

(65) Prior Publication Data

US 2018/0163002 A1  Jun. 14, 2018

Related U.S. Application Data

(63) Continuation of application No. 14/408,891, filed as application No. PCT/JP2013/065514 on Jun. 4, 2013, now Pat. No. 9,926,409.

(30) Foreign Application Priority Data

Jun. 25, 2012 (JP) .................. 2012-142168
Sep. 19, 2012 (JP) .................. 2012-206272

(51) Int. Cl.
| | |
|---|---|
| C08G 77/42 | (2006.01) |
| A61Q 5/06 | (2006.01) |
| A61K 8/898 | (2006.01) |
| C08F 283/12 | (2006.01) |
| A61K 8/91 | (2006.01) |
| A61Q 5/12 | (2006.01) |
| C08F 2/38 | (2006.01) |

(52) U.S. Cl.
CPC ............ *C08G 77/42* (2013.01); *A61K 8/898* (2013.01); *A61K 8/91* (2013.01); *A61Q 5/06* (2013.01); *A61Q 5/12* (2013.01); *C08F 283/12* (2013.01); *C08F 2/38* (2013.01)

(58) Field of Classification Search
None
See application file for complete search history.

(56) References Cited

U.S. PATENT DOCUMENTS

| | | | |
|---|---|---|---|
| 5,079,298 A | 1/1992 | Kuriyama et al. | |
| 5,468,477 A * | 11/1995 | Kumar | A61K 8/39 |
| | | | 424/49 |
| 5,805,264 A | 9/1998 | Janssen et al. | |
| 6,420,480 B1 | 7/2002 | Ozdeger | |
| 6,641,805 B1 | 11/2003 | Morita et al. | |
| 9,351,920 B2 | 5/2016 | Ohba et al. | |
| 9,926,409 B2 * | 3/2018 | Maekawa | A61Q 5/06 |
| 2002/0098214 A1 | 7/2002 | Adams et al. | |
| 2009/0087399 A1 | 4/2009 | Kuppert et al. | |
| 2012/0216823 A1 | 8/2012 | Fukuhara et al. | |
| 2012/0251605 A1 | 10/2012 | Iimura et al. | |

FOREIGN PATENT DOCUMENTS

| | | |
|---|---|---|
| JP | 61-283623 A | 12/1986 |
| JP | 6-49251 A | 2/1994 |
| JP | 11-269231 A | 10/1999 |
| JP | 2002-327064 A | 11/2002 |
| JP | 2003-532780 A | 11/2003 |
| JP | 3600623 B2 | 9/2004 |
| JP | 2010-540704 A | 12/2010 |
| JP | 2011-148784 A | 8/2011 |
| WO | WO 2011/062210 A1 | 5/2011 |

OTHER PUBLICATIONS

International Search Report, issued in PCT/JP2013/065514, dated Aug. 13, 2013.

* cited by examiner

*Primary Examiner* — Lakshmi S Channavajjala
(74) *Attorney, Agent, or Firm* — Birch, Stewart, Kolasch & Birch, LLP.

(57) ABSTRACT

The present invention relates to a organopolysiloxane graft polymer including an organopolysiloxane segment as a main chain thereof and an unsaturated monomer-derived polymer segment as a side chain thereof, in which the unsaturated monomer-derived polymer segment contains a repeating unit derived from N,N-dimethyl acrylamide in an amount of not less than 50% by mass and not more than 100% by mass, and a content of the organopolysiloxane segment in the organopolysiloxane graft polymer is not less than 10% by mass and not more than 70% by mass.

9 Claims, 1 Drawing Sheet

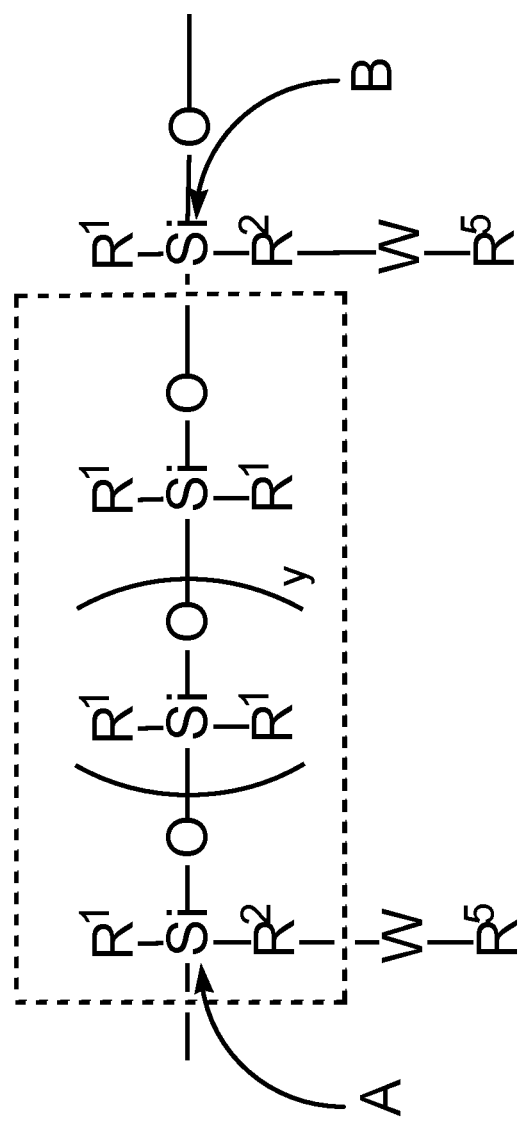

ORGANOPOLYSILOXANE GRAFT POLYMER

CROSS REFERENCE TO RELATED APPLICATIONS

This application is a Continuation of copending application Ser. No. 14/408,891, filed on Dec. 17, 2014, which was filed as a National Phase of PCT International Application No. PCT/JP2013/065514 on Jun. 4, 2013, which claims the benefit under 35 U.S.C. § 119(a) to Patent Application Nos. 2012-206272 and 2012-142168, filed in Japan on Sep. 19, 2012 and Jun. 25, 2012 respectively, all of which are hereby expressly incorporated by reference into the present application.

FIELD OF THE INVENTION

The present invention relates to an organopolysiloxane graft polymer, and more particularly, to an organopolysiloxane graft polymer that is useful as a hair cosmetic.

BACKGROUND OF THE INVENTION

Organopolysiloxanes have various excellent characteristics. Therefore, the organosiloxanes of various configurations have been used as a touch improver or the like which may be compounded in shampoos, hair conditioners, etc.

For example, Patent Literature 1 discloses a polyacryl-modified organopolysiloxane that is capable of imparting excellent gloss, luster and a feeling of smoothness to hair without stickiness and exhibiting a good hair style retentivity, and is free from accumulation on hair even when repeatedly used for a long period of time and any significant problem concerning formulation thereof.

In addition, Patent Literature 2 aims at providing a hairdressing method that is capable of imparting a soft touch and a natural finish feeling to hair, firmly fixing a hair style, maintaining the hair style for a long period of time without change even when exposed to external factors (such as combing of hand or fingers through hair, wind, vibrations, etc.), and further hairdressing the hair again, and discloses such a hairdressing method including the steps of applying a hair cosmetic containing a poly(N-acyl alkylene imine)-modified organopolysiloxane to hair, shaping the hair at a hair temperature of 50° C. or higher, and then cooling the hair to a temperature of lower than 50° C. to fix a style of the hair thus shaped.

CITATION LIST

Patent Literature

Patent Literature 1: JP 3600623B
Patent Literature 2: WO 2011/062210A

SUMMARY OF THE INVENTION

The polyacryl-modified organopolysiloxane described in Patent Literature 1 has such a problem that a film of the polyacryl-modified organopolysiloxane exhibits a low elastic modulus at room temperature, and therefore is insufficient in hair setting property and hair style retentivity. In addition, when the amount of the polyacryl-modified organopolysiloxane compounded in a hair cosmetic increases, there tends to arise such a problem that hair treated with the hair cosmetic suffers from a feeling of stickiness.

The poly(N-acyl alkylene imine)-modified organopolysiloxane described in Patent Literature 2 is produced by first subjecting a cyclic imino ether to living polymerization to obtain an end-reactive poly(N-acyl alkylene imine) and then connecting an organopolysiloxane segment (e.g., an amino-modified silicone) to the end-reactive poly(N-acyl alkylene imine). However, the living polymerization step and the connecting step require dehydration of a solvent or the like, and water or an alcohol solvent such as ethanol, etc., which can be compounded in a hair cosmetic, is unusable as a polymerization solvent in these steps. Therefore, since it is required to remove the polymerization solvent by drying, etc., there is a large burden on production of the above organopolysiloxane.

Further, in recent years, with the issuance of the regulation for emission of volatile organic compounds (VOC) in atmospheric air, etc., it has been required to have much consideration for environments, and there is an increasing demand for non-use of organic solvents. In the application fields of cosmetics, hair cosmetics, etc., it has also been demanded to reduce VOC, so that a base material to be compounded in the cosmetics, etc., has been required to exhibit a solubility or dispersibility in water.

The present invention aims at providing an organopolysiloxane graft polymer that has a high elastic modulus at room temperature, is capable of forming a film having a good touch feeling without stickiness, and exhibits a thermoplasticity as a property capable of being softened upon heating as well as a high dispersibility in water.

The present invention further aims at providing a hair cosmetic that can impart a soft touch feeling and a natural finish feeling to hair, can firmly fix a hair style without stickiness, and can maintain the hair style for a long period of time.

The present invention relates to the following organopolysiloxane graft polymer and hair cosmetic.

[1] An organopolysiloxane graft polymer including an organopolysiloxane segment as a main chain thereof and an unsaturated monomer-derived polymer segment as a side chain thereof, in which the unsaturated monomer-derived polymer segment contains a repeating unit derived from N,N-dimethyl acrylamide in an amount of not less than 50% by mass and not more than 100% by mass, and a content of the organopolysiloxane segment in the organopolysiloxane graft polymer is not less than 10% by mass and not more than 70% by mass.

[2] A hair cosmetic including the organopolysiloxane graft polymer according to the above aspect [1].

EFFECTS OF THE INVENTION

The organopolysiloxane graft polymer according to the present invention has a high elastic modulus at room temperature, exhibits a thermoplasticity as a property capable of being softened upon heating, and further has a high dispersibility in water. The hair cosmetic using the organopolysiloxane graft polymer according to the present invention is free from stickiness upon and after hair setting, and is excellent in hair setting capability and hair style retentivity after the hair setting.

BRIEF DESCRIPTION OF THE DRAWINGS

The FIGURE is a graphical representation of the "organopolysiloxane segment being present between the adjacent unsaturated monomer-derived polymer segments" as that term is used herein and means a portion surrounded by a broken line as shown in the FIGURE.

DETAILED DESCRIPTION OF THE INVENTION

[Organopolysiloxane Graft Polymer]

The organopolysiloxane graft polymer according to the present invention (hereinafter also referred to merely as a "graft polymer of the present invention") is a graft polymer including an organopolysiloxane segment as a main chain thereof and an unsaturated monomer-derived polymer segment as a side chain thereof, in which the unsaturated monomer-derived polymer segment contains a repeating unit derived from N,N-dimethyl acrylamide (hereinafter also referred to merely as "DMAAm") in an amount of not less than 50% by mass and not more than 100% by mass, and a content of the organopolysiloxane segment in the organopolysiloxane graft polymer is not less than 10% by mass and not more than 70% by mass.

In the graft polymer of the present invention, it is preferred that two or more side chains are respectively bonded to an optional silicon atom in the organopolysiloxane segment constituting the main chain of the graft polymer through an alkylene group containing a hetero atom, and it is more preferred that the two or more side chains are respectively bonded to one or more silicon atoms except for those silicon atoms bonded to both ends of the organopolysiloxane segment through the alkylene group, and it is still more preferred that the two or more side chains are respectively bonded to two or more silicon atoms except for those silicon atoms bonded to both ends of the organopolysiloxane segment through the alkylene group.

<Organopolysiloxane Segment>

The graft polymer of the present invention contains the organopolysiloxane segment as a main chain thereof.

The chemical structure of the organopolysiloxane segment is not particularly limited. Specific Examples of the preferred organopolysiloxane segment include modified organopolysiloxane segments represented by the following general formula (1) or (2).

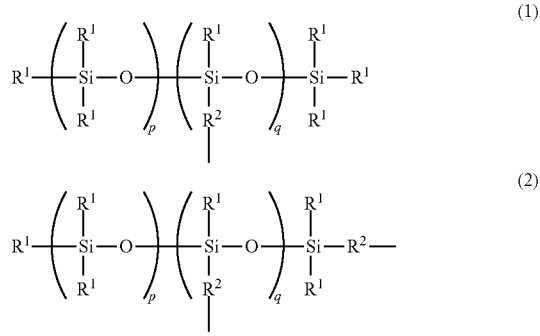

In the above general formulae (1) and (2), $R^1$ groups are each independently an alkyl group having not less than 1 and not more than 22 carbon atoms or an aryl group having not less than 6 and not more than 14 carbon atoms; and $R^2$ groups are each an alkylene group that may contain a hetero atom. Also, p is a number of not less than 2 and not more than 4,000, and q is a number of not less than 2 and not more than 250. In the general formulae (1) and (2), the repeating units in the number of p and the repeating units in the number of q may be bonded to each other either in a block form or in a random form.

In the above general formulae (1) and (2), the alkyl group represented by $R^1$ is a straight-chain alkyl group, a branched-chain alkyl group or a cyclic alkyl group. The number of carbon atoms of the alkyl group represented by $R^1$ is preferably not less than 1 and not more than 10, and more preferably not more than 6 from the viewpoint of a good water dispersibility of the graft polymer of the present invention. Specific examples of the alkyl group represented by $R^1$ include a methyl group, an ethyl group, an n-propyl group, an isopropyl group, an n-butyl group, a tert-butyl group, a pentyl group, a hexyl group, a cyclohexyl group, a heptyl group, an octyl group, a nonyl group, a decyl group, an undecyl group, a dodecyl group, an octadecyl group, a nonadecyl group, an eicosyl group and a docosyl group. Meanwhile, the water dispersibility of the graft polymer means such a property that the graft polymer can be stably dispersed in a composition containing water as a main component. When the graft polymer has a good water dispersibility, it is possible to compound the graft polymer in a hair cosmetic containing water a main solvent, so that the hair cosmetic can exhibit a good shampooing property.

The number of carbon atoms of the aryl group represented by $R^1$ is preferably not less than 6 and not more than 12, and more preferably not more than 9 from the viewpoint of a good water dispersibility of the graft polymer of the present invention. Specific examples of the aryl group represented by $R^1$ include a phenyl group, a tolyl group, a xylyl group, a naphthyl group, a biphenyl group, an anthryl group and a phenanthryl group.

Of these aryl groups as $R^1$, from the viewpoint of a good water dispersibility of the graft polymer of the present invention, preferred are straight-chain or branched-chain alkyl groups having not less than 1 and not more than 6 carbon atoms, more preferred are straight-chain or branched-chain alkyl groups having not less than 1 and not more than 3 carbon atoms, and still more preferred is a methyl group.

In the above general formulae (1) and (2), p is a number of not less than 2 and not more than 4,000, and q is a number of not less than 2 and not more than 250.

From the viewpoint of a good touch feeling (less stickiness) of hair after setting the hair with a hair cosmetic using the organopolysiloxane graft polymer of the present invention (hereinafter also referred to as a "hair cosmetic of the present invention"), p is preferably a number of not less than 50, more preferably not less than 80, and still more preferably not less than 100, and from the viewpoint of a good water dispersibility of the graft polymer of the present invention, p is also preferably a number of not more than 2,000, more preferably not more than 1300, and still more preferably not more than 700.

From the viewpoint of a good water dispersibility of the graft polymer of the present invention, q is preferably a number of not less than 3, and more preferably not less than 5, and from the viewpoints of a good hair setting property of the hair cosmetic of the present invention and a good hair style retentivity thereof after the setting, q is also preferably a number of not more than 50, and more preferably not more than 30.

In the above general formulae (1) and (2), a part or whole of the alkylene group ($R^2$) which may contain a hetero atom is bonded to both the main chain and the unsaturated monomer-derived polymer segment to function as a connecting group between the main chain and the unsaturated monomer-derived polymer segment as the side chain. In the case where any alkylene group that may contain a hetero atom is present in the form of a group unbonded to the unsaturated monomer-derived polymer segment, the alkylene group that may contain a hetero atom is bonded to the main chain and a hydrogen atom.

In the present invention, the number of carbon atoms of the alkylene group that may contain a hetero atom is preferably not less than 2, and more preferably not less than 3, from the viewpoint of a good availability of the raw materials used upon production of the graft polymer of the present invention. Also, from the viewpoint of a good water dispersibility of the graft polymer of the present invention, the number of carbon atoms of the alkylene group that may contain a hetero atom is preferably not more than 20, more preferably not more than 10, and still more preferably not more than 8.

In the present invention, the alkylene group that may contain a hetero atom may be interrupted by at least one atom or functional group selected from the group consisting of an oxygen atom, a sulfur atom, —NH—, —COO—, —NHCO— and —NR$^3$CO—. That is, the alkylene group that may contain a hetero atom may have a structure constituted of "-(an alkylene group portion 1)-(the above atom or functional group)-(an alkylene group portion 2)". In this case, the number of carbon atoms of the alkylene group means a sum of the number of carbon atoms of the alkylene group portion 1 and the number of carbon atoms of the alkylene group portion 2. In the above —NR$^3$CO—, R$^3$ is an alkyl group having not less than 1 and not more than 3 carbon atoms. When the alkylene group that may contain a hetero atom is interrupted by the above atom or functional group, from the viewpoint of facilitated production of the graft polymer of the present invention, the alkylene group that may contain a hetero atom is preferably interrupted by —NHCO—.

In the present invention, the alkylene group that may contain a hetero atom may be substituted with at least one monovalent group selected from the group consisting of a hydroxyl group, an amino group, a ($C_1$-$C_3$) alkyl amino group, a di-($C_1$-$C_3$) alkyl amino group, an amide group obtained by dehydration condensation of an amino group and a fatty acid having not less than 2 and not more than 4 carbon atoms, a carboxyl group, and a ($C_1$-$C_3$) alkyl ester group. In this case, the number of carbon atoms of the alkylene group that may contain a hetero atom does not include the number of carbon atoms contained in the above substituent group. From the viewpoint of a good availability of the raw materials upon production of the graft polymer of the present invention, the alkylene group that may contain a hetero atom is preferably substituted with at least one monovalent group selected from the group consisting of an acetamide group, a ($C_1$-$C_3$) alkyl amino group and an amine group.

In the present invention, the alkylene group that may contain a hetero atom may be substituted with a divalent hetero atom or a divalent group containing a hetero atom selected from the group consisting of —O—, —S—, —NH—, —NR$^{30}$—, and —COO—, in which R$^{30}$ is a ($C_1$-$C_3$) alkyl group that may be substituted with a dimethyl amino group. The divalent hetero atom or the divalent group containing a hetero atom is bonded to the unsaturated monomer-derived polymer segment when the alkylene group that may contain a hetero atom functions as a connecting group to the unsaturated monomer-derived polymer segment, and in otherwise cases, the divalent hetero atom or the divalent group containing a hetero atom is bonded to a hydrogen atom.

From the viewpoint of facilitated production of the graft polymer of the present invention, the alkylene group that may contain a hetero atom is preferably substituted with —S—.

The alkylene group (R$^2$) which may contain a hetero atom is preferably bonded to the unsaturated monomer-derived polymer segment through the hetero atom, more preferably through a nitrogen atom, an oxygen atom or a sulfur atom, and still more preferably through a sulfur atom.

Therefore, the "alkylene group that may contain a hetero atom" represented by R$^2$ corresponds to (i) an unsubstituted alkylene group; (ii) an alkylene group interrupted by at least one atom or functional group selected from the group consisting of an oxygen atom, a sulfur atom, —NH—, —COO—, —NHCO—, and —NR$^{30}$CO—; (iii) an alkylene group substituted with at least one monovalent group selected from the group consisting of a hydroxyl group, an amino group, a ($C_1$-$C_3$) alkyl amino group, a di-($C_1$-$C_3$) alkyl amino group, an amide group obtained by dehydration condensation of an amino group and a fatty acid having not less than 2 and not more than 4 carbon atoms, a carboxyl group, and a ($C_1$-$C_3$) alkyl ester group; (iv) an alkylene group substituted with a divalent hetero atom or a divalent group containing a hetero atom selected from the group consisting of —O—, —S—, —NH—, —NR$^{30}$—, and —COO—; and an alkylene group in the form of a combination of the above (ii), (iii) and (iv).

Specific examples of the alkylene group that may contain a hetero atom as used in the present invention include those group represented by the following formulae (i) to (xii). Of these groups, from the viewpoint of facilitated production of the graft polymer of the present invention, preferred are those groups represented by the following formulae (xi) and (xii).

(i)

(ii)

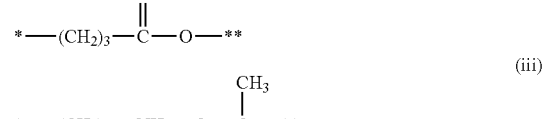

(iii)

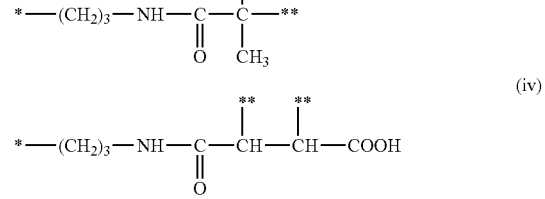

(iv)

(v)

(vi)

(vii)

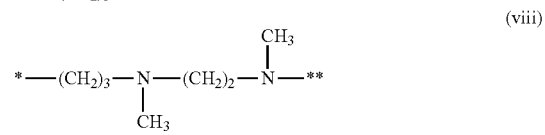

(viii)

-continued

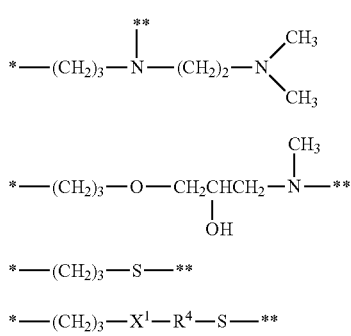

*—(CH$_2$)$_3$—S—**  (xi)

*—(CH$_2$)$_3$—X$^1$—R$^4$—S—**  (xii)

In the formulae (i) to (xii), "*" represents a moiety bonded to the silicon atom in the general formula (1) or (2), whereas "**" represents a moiety bonded to the unsaturated monomer-derived polymer segment.

In the formula (xii), X$^1$ is at least one group selected from the group consisting of —O—, —OCO—, —COO—, —CONH—, and —NHCO—. Of these groups, from the viewpoint of facilitated production of the graft polymer of the present invention, preferred are —CONH— and —NHCO—, and more preferred is —NHCO—.

Also, in the formula (xii), R$^4$ is an alkylene group that may be substituted with at least one monovalent group selected from the group consisting of a hydroxyl group, an amino group, a (C$_1$-C$_3$) alkyl amino group, a di-(C$_1$-C$_3$) alkyl amino group, an amide group obtained by dehydration condensation of an amino group and a fatty acid having not less than 2 and not more than 4 carbon atoms, a carboxyl group, and a (C$_1$-C$_3$) alkyl ester group. Of these substituent groups, from the viewpoint of a good availability of the raw materials upon production of the graft polymer, preferred are an acetamide group, a (C$_1$-C$_3$) alkyl amino group and an amino group. The number of carbon atoms of the alkylene group represented by R$^4$ is preferably not less than 2 and more preferably not less than 3, from the viewpoint of facilitated production of the graft polymer of the present invention, and also is preferably not more than 10 and more preferably not more than 6, from the viewpoint of a good water dispersibility of the graft polymer of the present invention.

Specific examples of R$^4$ include those groups represented by the following formulae (xiii) to (xv).

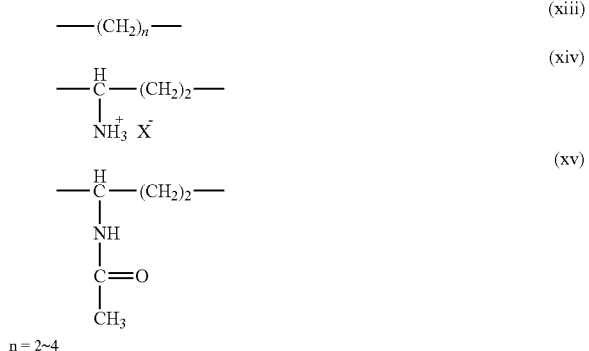

In the formula (xiv), X$^-$ represents an anion selected from the group consisting of a halide ion such as a chloride ion and a bromide ion, an acetate ion and a (C$_1$-C$_3$) alkyl sulfate ion.

<Unsaturated Monomer-Derived Polymer Segment>

The organopolysiloxane graft polymer of the present invention contains an unsaturated monomer-derived polymer segment as a side chain thereof. From the viewpoint of a good water dispersibility of the graft polymer of the present invention, the unsaturated monomer-derived polymer segment contains a repeating unit derived from DMAAm in an amount of not less than 50% by mass, preferably not less than 70% by mass, and more preferably not less than 75% by mass. Also, from the viewpoint of reducing stickiness of hair after setting the hair using the hair cosmetic of the present invention, the content of the repeating unit derived from DMAAm in the unsaturated monomer-derived polymer segment is not more than 100% by mass, preferably not more than 95% by mass, and more preferably not more than 90% by mass.

The repeating unit derived from the unsaturated monomer as used in the present invention means a repeating unit formed upon polymerization of the unsaturated monomer.

In the graft polymer of the present invention, the content of the repeating unit derived from DMAAm in the unsaturated monomer-derived polymer segment may be measured by an NMR method.

The moiety other than the repeating unit derived from DMAAm in the unsaturated monomer-derived polymer segment is constituted of a repeating unit derived from an unsaturated monomer (except for DMAAm) capable of copolymerizing with DMAAm. Examples of the repeating unit derived from the unsaturated monomer capable of copolymerizing with DMAAm include those repeating units derived from unsaturated monomers such as olefins, halogenated olefins, vinyl esters, (meth)acrylic acid esters, and (meth)acrylamides (except for DMAAm). The moiety other than the repeating unit derived from DMAAm in the unsaturated monomer-derived polymer segment may be constituted of either a repeating unit derived from a single kind of unsaturated monomer capable of copolymerizing with DMAAm, or a repeating unit derived from two or more kinds of unsaturated monomers capable of copolymerizing with DMAAm.

Specific examples of the olefins include ethylene, propylene and isobutylene. Specific examples of the halogenated olefins include vinyl chloride, vinyl fluoride, vinylidene chloride and vinylidene fluoride. Specific examples of the vinyl esters include vinyl formate, vinyl acetate, vinyl propionate and vinyl versatate.

Specific examples of the (meth)acrylic acid esters include (meth)acrylic acid esters containing an alkyl group having not less than 1 and not more than 16 carbon atoms such as methyl (meth)acrylate, ethyl (meth)acrylate, propyl (meth)acrylate, isobutyl (meth)acrylate, n-butyl (meth)acrylate, tert-butyl (meth)acrylate, hexyl (meth)acrylate, octyl (meth)acrylate, 2-ethylhexyl (meth)acrylate, decyl (meth)acrylate, dodecyl (meth)acrylate and cyclohexyl (meth)acrylate; (meth)acrylic acid esters containing an alkyl group having not less than 1 and not more than 16 carbon atoms which is substituted with a hydroxyl group, such as 2-hydroxyethyl (meth)acrylate; and polyethylene glycol (meth)acrylate, polyethylene glycol monomethyl ether (meth)acrylate, etc.

Specific examples of the (meth)acrylamides except for DMAAm include (meth)acrylamides such as acrylamide and methacrylamide; N,N-dialkyl (meth)acrylamides (except for DMAAm) such as N,N-diethyl (meth)acrylamide; N-alkyl (meth)acrylamides such as N-isopropyl (meth)acrylamide, N-tert-butyl (meth)acrylamide, N-cyclohexyl (meth)acrylamide and N-tert-octyl (meth)acrylamide; N-mono-substituted (meth)acrylamides containing a carbonyl group in a substituent group bonded to a nitrogen atom thereof, such as diacetone (meth)acrylamide; N-mono-substituted (meth)acrylamides containing an amino group in a substituent group bonded to a nitrogen atom thereof, such as N,N-dimethylaminopropyl (meth)acrylamide; and N-mono-substituted (meth)acrylamides containing a hydroxyl group in a substituent group bonded to a nitrogen atom thereof, such as N-methylol (meth)acrylamide and N-hydroxyethyl (meth)acrylamide.

Of these unsaturated monomers, from the viewpoints of a good hair setting property and a good hair style retentivity after the hair setting, preferred are (meth)acrylamides except for DMAAm and/or (meth)acrylates; more preferred are acrylamide, methacrylamide, N,N-diethyl (meth)acrylamide, N-isopropyl (meth)acrylamide, N-tert-butyl (meth)acrylamide, diacetone (meth)acrylamide, N,N-dimethylaminopropyl (meth)acrylamide, N-hydroxyethyl (meth)acrylamide, N-methylol (meth)acrylamide, methyl (meth)acrylate, ethyl (meth)acrylate, propyl (meth)acrylate, isobutyl (meth)acrylate, n-butyl (meth)acrylate, tert-butyl (meth)acrylate and 2-hydroxyethyl (meth)acrylate; still more preferred are N-tert-butyl (meth)acrylamide, N-hydroxyethyl (meth)acrylamide, diacetone (meth)acrylamide, methyl (meth)acrylate, ethyl (meth)acrylate, tert-butyl (meth)acrylate and N,N-dimethylaminopropyl (meth)acrylamide; even still more preferred are N-tert-butyl (meth)acrylamide, N-hydroxyethyl (meth)acrylamide, diacetone (meth)acrylamide, methyl (meth)acrylate, ethyl (meth)acrylate and tert-butyl (meth)acrylate; and further even still more preferred is N-tert-butyl (meth)acrylamide.

<Construction of Organopolysiloxane Graft Polymer>

The content of the organopolysiloxane segment in the graft polymer of the present invention is not less than 10% by mass, preferably not less than 20% by mass, and more preferably not less than 30% by mass, from the viewpoint of reducing stickiness of hair after setting the hair using the hair cosmetic of the present invention, and is also not more than 70% by mass, preferably not more than 60% by mass, and more preferably not more than 50% by mass, from the viewpoint of a good water dispersibility of the graft polymer of the present invention.

The content of the organopolysiloxane segment in the graft polymer of the present invention may be measured by an NMR method.

In addition, from the viewpoints of attaining a good water dispersibility of the graft polymer of the present invention and reducing stickiness of hair after setting the hair using the hair cosmetic of the present invention, the mass ratio (a/b) of the organopolysiloxane segment (a) to the unsaturated monomer-derived polymer segment (b) is preferably not less than 10/90, more preferably not less than 20/80, still more preferably not less than 30/70, and even still more preferably not less than 35/65, and is also preferably not more than 70/30, more preferably not more than 60/40, and still more preferably not more than 50/50.

Meanwhile, in the present specification, when the graft polymer of the present invention is produced from the below-mentioned radical-reactive organopolysiloxane, the above mass ratio (a/b) is regarded as being the same as a ratio (c/(d−e)) of a "total amount (c) of the radical-reactive organopolysiloxane charged upon production of the graft polymer" to a value obtained by subtracting a "total amount (e) of a polymer derived from an unsaturated monomer which is unbonded to the organopolysiloxane produced upon production of the graft polymer" from a "total amount (d) of the unsaturated monomer charged upon production of the graft polymer" (the following formula (I)).

$$a/b = c/(d-e) \tag{I}$$

The number-average molecular weight (MNg) of the organopolysiloxane segment being present between the adjacent unsaturated monomer-derived polymer segments (hereinafter also referred to merely as a "molecular weight between graft points") is preferably not less than 500, more preferably not less than 700, still more preferably not less than 1,000, and even still more preferably not less than 1,500, from the viewpoints of attaining a good hair setting property when setting the hair with a hair cosmetic containing the organopolysiloxane graft polymer of the present invention and improving a hair style retentivity after the setting, and is also preferably not more than 10,000, more preferably not more than 5,000, still more preferably not more than 3,000, and even still more preferably not more than 2,500, from the viewpoint of attaining a good water dispersibility of the graft polymer of the present invention.

The "organopolysiloxane segment being present between the adjacent unsaturated monomer-derived polymer segments" as used herein means a portion surrounded by a broken line as shown in the FIGURE which is located between a bonding point (bonding point A) at which the unsaturated monomer-derived polymer segment is bonded to the organopolysiloxane segment and a bonding point (bonding point B) at which the unsaturated monomer-derived polymer segment adjacent to the above polymer segment is bonded to the organopolysiloxane segment, and is constituted of one $R^1SiO$ unit, one $R^2$ group and $R^1{}_2SiO$ units in the number of y+1.

In the FIGURE, $R^1$ groups are each independently an alkyl group having not less than 1 and not more than 22 carbon atoms or an aryl group having not less than 6 and not more than 14 carbon atoms; $R^2$ groups are each an alkylene group that may contain a hetero atom; —W—$R^5$ groups are each an unsaturated monomer-derived polymer segment in which $R^5$ is a residue of a polymerization initiator or a hydrogen atom; and y is a positive number.

The molecular weight between graft points is an average value of molecular weights of the portions surrounded by a broken line in the FIGURE, and may be construed as a mass (g/mol) of the organopolysiloxane segment per one mole of the unsaturated monomer-derived polymer segment. In the case where the graft polymer of the present invention is produced from the below-mentioned radical-reactive organopolysiloxane, and all of the radical-reactive functional groups are bonded to the unsaturated monomer-derived polymer segment, the molecular weight between graft points is also regarded as being identical to an inverse number of a molar number (mol/g) of the radical-reactive functional groups that are present per a unit mass of the radical-reactive organopolysiloxane.

In addition, the weight-average molecular weight (MWsi) of the organopolysiloxane segment constituting the main chain of the graft polymer is preferably not less than 3,000, more preferably not less than 5,000, still more preferably not less than 10,000, and even still more preferably not less than 15,000, from the viewpoints of a good hair setting property when setting the hair using a hair cosmetic containing the organopolysiloxane graft polymer of the present invention and a good hair style retentivity after the setting. Also, MWsi is preferably not more than 200,000, more preferably not more than 100,000, still more preferably not more than 60,000, and even still more preferably not more than 50,000, from the viewpoint of a good water dispersibility of the graft polymer of the present invention.

In the case where the organopolysiloxane graft polymer of the present invention is produced from the below-mentioned radical-reactive organopolysiloxane, the organopolysiloxane segment has a structure common to that of the radical-reactive organopolysiloxane, and therefore MWsi is substantially the same as a weight-average molecular weight (MWra) of the radical-reactive organopolysiloxane. For this reason, in the present invention, MWsi is regarded as being the same as MWra. Meanwhile, MWra is a value calculated in terms of a polystyrene from such a molecular weight as measured by a gel permeation chromatography (GPC) under the measuring conditions described below in Examples.

The weight-average molecular weight (MWt) of the graft polymer of the present invention is preferably not less than 10,000, more preferably not less than 14,000, still more preferably not less than 17,000, and even still more preferably not less than 30,000, from the viewpoints of a good hair setting property when setting the hair using a hair cosmetic containing the organopolysiloxane graft polymer of the present invention and a good hair style retentivity after the setting. Also, MWt is preferably not more than 200,000, more preferably not more than 160,000, still more preferably not more than 130,000, and even still more preferably not more than 95,000, from the viewpoint of a good water dispersibility of the graft polymer of the present invention. When MWt falls within the above-specified range, it is possible to ensure a sufficient strength of a film obtained from the graft polymer, and the resulting graft polymer can exhibit an excellent water dispersibility and can be further improved in hair setting property and hair style retentivity after setting without stickiness.

In the present specification, MWt is a value calculated in terms of a polystyrene from such a molecular weight as measured by GPC under the measuring conditions described below in Examples.

In addition, when producing the graft polymer of the present invention from the radical-reactive organopolysiloxane, the weight-average molecular weight as a calculated value (MWtcalc) of the graft polymer of the present invention which is calculated from MWra and an inverse number of the above mass ratio (a/b) according to the following formula (II), is preferably not less than 10,000, more preferably not less than 14,000, still more preferably not less than 17,000, and even still more preferably not less than 30,000, from the viewpoints of a good hair setting property when setting the hair using a hair cosmetic containing the organopolysiloxane graft polymer of the present invention and a good hair style retentivity after the setting. Also, MWtcalc is preferably not more than 200,000, more preferably not more than 160,000, still more preferably not more than 130,000, and even still more preferably not more than 95,000, from the viewpoint of a good water dispersibility of the graft polymer of the present invention.

$$MWtcalc = MWra \div \{1+\text{mass ratio}(b/a)\} \tag{II}$$

<Process for Producing Organopolysiloxane Graft Polymer>

Next, the method for producing the graft polymer of the present invention is described. The method for producing the graft polymer of the present invention is not particularly limited. For example, there may be used (i) a graft-onto method (polymer reaction method) in which an organopolysiloxane containing a reactive functional group is reacted with an unsaturated monomer-derived polymer segment containing an end functional group capable of reacting the reactive functional group; (ii) a graft-from method in which the unsaturated monomer is subjected to radical polymerization in the presence of the below-mentioned radical-reactive organopolysiloxane; or the like. Of these methods, from the viewpoint of reducing a burden upon production of the graft polymer, preferred is (ii) the graft-from method in which the unsaturated monomer is subjected to radical polymerization in the presence of the radical-reactive organopolysiloxane. In the following, the method for producing the graft polymer of the present invention by the graft-from method is described.

(Radical-Reactive Organopolysiloxane)

The graft polymer of the present invention can be produced by subjecting the unsaturated monomer to radical polymerization in the presence of the radical-reactive organopolysiloxane represented by the following general formula (4) or (5).

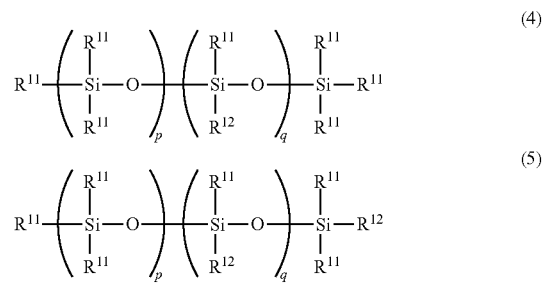

In the above general formulae, $R^{11}$ groups are each independently an alkyl group having not less than 1 and not more than 22 carbon atoms or an aryl group having not less than 6 and not more than 14 carbon atoms; and $R^{12}$ groups are each an alkyl group containing a radical-reactive functional group (hereinafter also referred to as a "radical reactive group-containing alkyl group").

The preferred form of $R^{11}$ in the above general formulae (4) and (5) is the same as the preferred form of $R^1$ in the above general formulae (1) and (2).

The suffixes p and q in the above general formulae (4) and (5) have the same meanings as p and q in the above general formulae (1) and (2), and the preferred forms of p and q in the above general formulae (4) and (5) are the same as the preferred forms of p and q in the above general formulae (1) and (2).

The radical-reactive functional group as used in the present invention means a functional group capable of generating a radical. Examples of the radical-reactive functional group include an ethylenically unsaturated group, a halogeno group such as a chloro group and a bromo group, and a sulfanyl group (mercapto group). Of these functional groups, a sulfanyl group is preferred from the viewpoints of a high reactivity with the unsaturated monomer and a well-controlled molecular weight of the resulting polymer.

In the above general formulae (4) and (5), the number of carbon atoms of the radical-reactive group-containing alkyl group represented by $R^{12}$ is preferably not less than 2, and more preferably not less than 3, from the viewpoint of a good availability of the radical-reactive organopolysiloxane, and is also preferably not more than 20, more preferably not more than 10, and still more preferably not more than 8, from the viewpoint of a good water dispersibility of the graft polymer of the present invention.

Meanwhile, in the present invention, the number of carbon atoms of the radical-reactive group-containing alkyl group does not include the number of carbon atoms of the radical-reactive functional group even though the radical-reactive functional group contains any carbon atoms, and also does not include the number of carbon atoms of the monovalent substituent group even though the radical-reactive group-containing alkyl group is substituted therewith.

In the above general formulae (4) and (5), the radical-reactive group-containing alkyl group represented by $R^{12}$ may be substituted with at least one monovalent group selected from the group consisting of a hydroxyl group, an amino group, a ($C_1$-$C_3$) alkyl amino group, a di-($C_1$-$C_3$) alkyl amino group, an amide group obtained by dehydration condensation of an amino group and a fatty acid having not less than 2 and not more than 4 carbon atoms, a carboxyl group, and a ($C_1$-$C_3$) alkyl ester group. Of these monovalent substituent groups, from the viewpoint of a good availability of the raw materials upon production of the radical-reactive organopolysiloxane, preferred are an acetamide group, a ($C_1$-$C_3$) alkyl amino group and an amino group.

In the above general formulae (4) and (5), the radical-reactive group-containing alkyl group represented by $R^{12}$ may be interrupted by at least one atom or functional group selected from the group consisting of an oxygen atom, a sulfur atom, —NH—, —COO—, —NHCO— and —$NR^{13}$CO—. In the above —$NR^{13}$CO—, $R^{13}$ is an alkyl group having not less than 1 and not more than 3 carbon atoms. When the radical-reactive group-containing alkyl group is interrupted by the above atom or functional group, from the viewpoints of a good availability and facilitated production of the radical-reactive organopolysiloxane, the radical-reactive group-containing alkyl group is preferably interrupted by —NHCO—.

Specific examples of the radical-reactive group-containing alkyl group used in the present invention includes those groups represented by the following formulae (xvii) to (xx). Of these groups, from the viewpoints of facilitated production and a good availability of the radical-reactive organopolysiloxane, preferred are those groups represented by the following formula (xix) or (xx). $X^{11}$ and $R^{14}$ in the formula (xx) as well as the preferred forms thereof are the same as $X^1$ and $R^4$ in the formula (xii) as well as the preferred forms thereof.

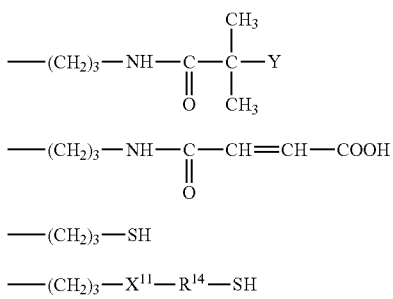

In the present invention, the weight-average molecular weight (MWra) of the radical-reactive organosiloxane is regarded as being the same as the weight-average molecular weight (MWsi), and therefore the preferred form of MWra is the same as the preferred form of MWsi.

Meanwhile, MWra used in the present invention is a value calculated in terms of a polystyrene from such a molecular weight as measured by GPC under the measuring conditions described below in Examples.

The number of moles of the radical-reactive functional group being present per a unit mass of the radical-reactive organopolysiloxane is preferably not more than 1/500 mol/g, more preferably not more than 1/700 mol/g, and still more preferably not more than 1/1,000 mol/g, from the viewpoints of attaining a good hair setting property when setting the hair with a hair cosmetic containing the organopolysiloxane graft polymer of the present invention and improving a hair style retentivity after the setting, and is also preferably not less than 1/10,000 mol/g, more preferably not less than 1/5,000 mol/g, and still more preferably not less than 1/3,000 mol/g, from the viewpoint of a good water dispersibility of the graft polymer of the present invention.

The radical-reactive organopolysiloxane containing a sulfanyl group as the radical-reactive group may be commercially available, and examples of the commercially available radical-reactive organopolysiloxane include "KF-2001" (available from Shin-Etsu Chemical Co., Ltd.), etc.

(Reactive Functional Group-Containing Organopolysiloxane)

The radical-reactive organopolysiloxane may also be produced by reacting a reactive functional group-containing organopolysiloxane represented by the following general formula (6) or (7) with a radical reactivity-imparting agent. The reactive functional group-containing organopolysiloxane represented by the following general formula (6) or (7) is readily commercially available as products having various structures.

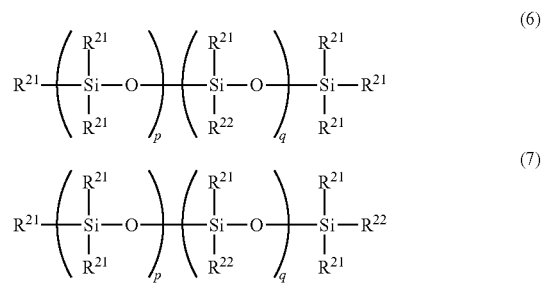

In the above general formulae (6) and (7), $R^{21}$ groups are each independently an alkyl group having not less than 1 and not more than 22 carbon atoms or an aryl group having not less than 6 and not more than 14 carbon atoms; and $R^{22}$ groups are each an alkyl group containing a reactive functional group (hereinafter also referred to as a "reactive group-containing alkyl group"). The suffixes p and q in the above general formulae (6) and (7) have the same meanings as p and q in the above general formulae (4) and (5), and the preferred forms of p and q in the above general formulae (6) and (7) are the same as the preferred forms of p and q in the above general formulae (4) and (5).

The preferred form of $R^{21}$ in the above general formulae (6) and (7) is the same as the preferred form of $R^1$ in the above general formulae (4) and (5).

The reactive functional group as used in the present invention means a hydroxyl group, an amino group, a carboxyl group or an epoxy group.

The reactive functional group-containing organopolysiloxane contains at least one substituent group selected from the group consisting of a hydroxyl group, an amino group, a carboxyl group and an epoxy group.

Of these reactive functional groups, from the viewpoint of a good availability, preferred are a hydroxyl group, an amino group and an epoxy group, and from the viewpoints of a high reactivity and a good handling property, preferred is an amino group.

In the above general formulae (6) and (7), the number of carbon atoms of the reactive group-containing alkyl group represented by $R^{22}$ is preferably not less than 2, and more preferably not less than 3, form the viewpoint of a good availability of the reactive functional group-containing organopolysiloxane, and is also preferably not more than 15, more preferably not more than 10, and still more preferably not more than 5, from the viewpoint of a good water dispersibility of the graft polymer of the present invention.

Specific examples of the reactive group-containing alkyl group include those groups represented by the following formulae (xxi) to (xxviii). Of these reactive group-containing alkyl groups, from the viewpoint of a good availability, preferred is at least one reactive group-containing alkyl group selected from the group consisting of those groups represented by the formulae (xxi) to (xxiv), and from the viewpoint of a high reactivity, more preferred is the reactive group-containing alkyl group represented by the formula (xxiv).

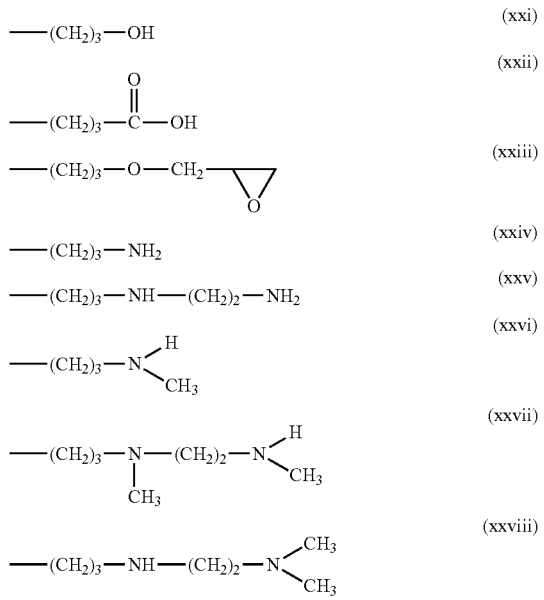

The weight-average molecular weight (MWsim) of the reactive functional group-containing organopolysiloxane is preferably not less than 3,000, more preferably not less than 5,000, still more preferably not less than 10,000, and even still more preferably not less than 15,000, from the viewpoints of attaining a good hair setting property when setting the hair with a hair cosmetic containing the organopolysiloxane graft polymer of the present invention and improving a hair style retentivity after the setting, and is also preferably not more than 200,000, more preferably not more than 100,000, still more preferably not more than 60,000, and even still more preferably not more than 50,000, from the viewpoint of a good water dispersibility of the graft polymer of the present invention.

Meanwhile, MWsim used in the present invention is a value calculated in terms of a polystyrene from such a molecular weight as measured by GPC under the measuring conditions described below in Examples.

The number of moles of the reactive functional group being present per a unit mass of the reactive functional group-containing organopolysiloxane is preferably not more than 1/500 mol/g, more preferably not more than 1/700 mol/g, and still more preferably not more than 1/1,000 mol/g, from the viewpoints of attaining a good hair setting property when setting the hair with a hair cosmetic containing the organopolysiloxane graft polymer of the present invention and improving a hair style retentivity after the setting, and is also preferably not less than 1/10,000 mol/g, more preferably not less than 1/5,000 mol/g, and still more preferably not less than 1/3,000 mol/g, from the viewpoint of a good water dispersibility of the graft polymer of the present invention.

(Radical Reactivity-Imparting Agent)

The radical reactivity-imparting agent as used in the present invention means an agent capable of reacting with the reactive functional group of the reactive functional group-containing organopolysiloxane to add a radical-reactive functional group to the reactive functional group-containing organopolysiloxane.

As the radical reactivity-imparting agent, there may be used those compounds containing a radical-reactive functional group and at least one functional group capable of reacting with the reactive functional group of the above reactive functional group-containing organopolysiloxane which is selected from the group consisting of a carboxyl group, an ester group, an epoxy group, a hydroxyl group and lactones, in a molecule thereof. In the case where the reactive functional group of the above reactive functional group-containing organopolysiloxane is a hydroxyl group, an amino group or an epoxy group, unsubstituted or substituted thiolactones may be used as the radical reactivity-imparting agent.

The radical-reactive functional group of the radical reactivity-imparting agent and the preferred form thereof are the same as the radical-reactive functional group of the radical-reactive organopolysiloxane and the preferred form thereof. Of these radical reactivity-imparting agents, from the viewpoint of a high reactivity upon polymerization, preferred are those radical reactivity-imparting agents containing a sulfanyl group (mercapto group) as the radical-reactive functional group, for example, compounds containing a sulfanyl group and a carboxyl group in a molecule thereof such as 3-mercapto propionic acid, and lactones containing a sulfanyl group such as γ-butyrolactone thiol. Also, as the unsubstituted or substituted thiolactones, there may be mentioned γ-thiobutyrolactone, N-acetyl-DL-homocysteine thiolactone, DL-homocysteine thiolactone hydrochloride, or the like. Of these radical reactivity-imparting agents, from the viewpoints of a good reactivity with the reactive organopolysiloxane and a high reactivity upon the polymerization, more preferred is N-acetyl-DL-homocysteine thiolactone.

The amount of the radical reactivity-imparting agent used is preferably not less than 0.8 equivalent, and more preferably not less than 0.9 equivalent, from the viewpoint of a high reactivity, and is also preferably not more than 1.2 equivalent, and more preferably not more than 1.1 equivalent, from the viewpoint of reducing an amount of the radical reactivity-imparting agent remaining unreacted after the reaction, on the basis of a total amount of the reactive functional group of the reactive functional group-containing organopolysiloxane.

(Production of Radical-Reactive Organopolysiloxane)

The reaction between the radical reactivity-imparting agent and the reactive functional group-containing organopolysiloxane may be carried out in the presence of a solvent.

Examples of the solvent include water; alcohols such as methanol, ethanol and isopropanol; ketones such as acetone and methyl ethyl ketone; esters such as ethyl acetate and butyl acetate; hydrocarbons such as hexane and cyclohexane; ethers such as diethyl ether and tetrahydrofuran; aromatic compounds such as benzene and toluene; and halogenated hydrocarbons such as dichloromethane and chloroform.

From the viewpoint of reducing an environmental burden, it is preferred that no solvent is used on the above reaction.

The reaction temperature is preferably not lower than 70° C., and more preferably not lower than 90° C., from the viewpoint of a high reactivity, and is also preferably not higher than 200° C., and more preferably not higher than 150° C., from the viewpoint of a good chemical stability of the resulting radical-reactive polysiloxane.

The reaction time is preferably not less than 1 h, and more preferably not less than 2 h, from the viewpoint of allowing the reaction to proceed sufficiently, and is also preferably not more than 10 h, and more preferably not more than 5 h, from the viewpoint of a good productivity.

From the viewpoint of a high reactivity of the resulting radical-reactive organopolysiloxane, the reaction between the reactive functional group-containing organopolysiloxane and the radical reactivity-imparting agent is preferably carried out until a conversion rate of at least one of the reactive functional group of the reactive functional group-containing organopolysiloxane and the radical reactivity-imparting agent reaches not less than 80%, and more preferably not less than 90%.

The method of measuring the respective conversion rates may vary depending upon the reactive functional group of the reactive functional group-containing organopolysiloxane and the radical reactivity-imparting agent used in the reaction, and any of the conversion rates may be measured by known methods. For example, in the case where the reactive functional group of the reactive functional group-containing organopolysiloxane is an amino group, and the radical reactivity-imparting agent is a thiolactone, the conversion rate of the amino group may be determined by "Testing Method for Total Base Number of Petroleum Products (perchlorate method)" (JIS K2501), and the conversion rate of the thiolactone may be determined by a liquid chromatography.

(Production of Organopolysiloxane Graft Polymer)

The method of subjecting the unsaturated monomer to polymerization in the presence of the radical-reactive organopolysiloxane is not particularly limited, and there may be adopted a bulk polymerization method, a solution polymerization method and a suspension polymerization method, etc. Of these polymerization methods, preferred is a solution polymerization method.

The amount of the unsaturated monomer used as the raw material is preferably not less than 30% by mass, more preferably not less than 40% by mass, and still more preferably not less than 50% by mass, on the basis of a total amount of the radical-reactive organopolysiloxane and the unsaturated monomer as the raw materials, from the viewpoint of a good water dispersibility of the graft polymer of the present invention. Also, from the viewpoint of reducing stickiness of hair after setting the hair with a hair cosmetic containing the organopolysiloxane graft polymer of the present invention, the amount of the unsaturated monomer used is preferably not more than 90% by mass, more preferably not more than 80% by mass, and still more preferably not more than 70% by mass, on the basis of a total amount of the radical-reactive organopolysiloxane and the unsaturated monomer as the raw materials.

The content of DMAAm in the unsaturated monomer as the raw material is preferably not less than 50% by mass, more preferably not less than 70% by mass, and still more preferably not less than 75% by mass, from the viewpoint of a good water dispersibility of the graft polymer of the present invention, and is also preferably not more than 100% by mass, more preferably not more than 95% by mass, and still more preferably not more than 90% by mass, from the viewpoint of reducing stickiness of hair after setting the hair with a hair cosmetic containing the organopolysiloxane graft polymer of the present invention.

In the case where the content of DMAAm in the unsaturated monomer is not 100% by mass, the unsaturated monomer may contain an unsaturated monomer (except for DMAAm) capable of copolymerizing with DMAAm.

Specific examples of the above unsaturated monomer and the preferred form thereof are the same as the specific examples of the above unsaturated monomer capable of copolymerizing with DMAAm and the preferred form thereof.

In the case where the unsaturated monomer is polymerized by a solution polymerization method, the solvent used therein is not particularly limited as long as any of the radical-reactive organopolysiloxane and the unsaturated monomer as the raw materials as well as the obtained graft polymer of the present invention can be dissolved or uniformly dispersed therein.

Specific examples the solvent include water; alcohols such as methanol, ethanol and isopropanol; ketones such as acetone and methyl ethyl ketone; esters such as ethyl acetate and butyl acetate; hydrocarbons such as hexane and cyclohexane; ethers such as diethyl ether and tetrahydrofuran; aromatic compounds such as benzene and toluene; and halogenated hydrocarbons such as dichloromethane and chloroform. These solvent may be used alone or in combination of any two or more thereof.

Of these solvents, from the viewpoint of obtaining the graft polymer of the present invention which has a more uniform side chain molecular weight distribution, it is preferred to use at least one solvent selected from the group consisting of water; alcohols having not less than 1 and not more than 8 carbon atoms such as ethanol and isopropanol; esters having not less than 2 and not more than 8 carbon atoms such as ethyl acetate and butyl acetate; and ethers having not less than 2 and not more than 8 carbon atoms such as diethyl ether and tetrahydrofuran. Further, from the viewpoint of bringing the solvent used upon production of the graft polymer of the present invention into cosmetic products when using the graft polymer of the present invention in the applications of a hair cosmetic, etc., it is more preferred to use at least one solvent selected from the group consisting of water, and alcohols having not less than 1 and not more than 3 carbon atoms such as ethanol.

The amount of the solvent used is is not particularly limited as long as any of the radical-reactive organopolysiloxane and the unsaturated monomer as the raw materials as well as the obtained organopolysiloxane graft polymer of the present invention can be dissolved or uniformly dispersed therein. From the viewpoints of a facilitated operation upon production of the graft polymer and a high productivity thereof, the amount of the solvent used is preferably not less than 20% by mass, more preferably not less than 40% by mass, still more preferably not less than 60% by mass, and even still more preferably not less than 100% by mass, on the basis of a total amount of the radical-reactive organopolysiloxane and the unsaturated monomer charged upon the production. Also, from the viewpoint of a high reactivity, the amount of the solvent used is preferably not more than 1,000% by mass, more preferably not more than 900% by mass, still more preferably not more than 400% by mass, and even still more preferably not more than 300% by mass, on the basis of a total amount of the radical-reactive organopolysiloxane and the unsaturated monomer charged upon the production.

Examples of the polymerization initiator include azo-based initiators such as 2,2'-azobisisobutyronitrile and 2,2'-azobis(2,4-dimethyl valeronitrile); peroxide-based initiators such as lauroyl peroxide and benzoyl peroxide; and persulfate-based initiators such as ammonium persulfate. Also, the polymerization may be initiated by generating a radical by irradiation of light, etc. Of these polymerization initiators, from the viewpoint of a high reactivity, preferred is 2,2'-azobis(2,4-dimethyl valeronitrile). The amount of the polymerization initiator used is not particularly limited. The amount of the polymerization initiator used is preferably not more than 10% by mass, and more preferably not more than 1% by mass, on the basis of a total amount of the unsaturated monomer charged, from the viewpoint of a weight-average molecular weight of the resulting graft polymer of the present invention, and is also preferably not less than 0.001% by mass, and more preferably not less than 0.01% by mass, on the basis of a total amount of the unsaturated monomer charged, from the viewpoint of a high reactivity.

The temperature used upon the polymerization reaction may be appropriately selected according to the kinds of polymerization initiator and solvent used, etc., and is preferably not lower than 50° C., and more preferably not lower than 60° C., from the viewpoint of a high polymerization reaction rate. The polymerization reaction is preferably carried out under a normal pressure in order to reduce a burden on facilities used for the polymerization reaction. From the viewpoint of carrying out the reaction at a temperature not higher than a boiling point of the solvent, the temperature used upon the polymerization reaction is preferably not higher than 100° C., and more preferably not higher than 90° C.

The polymerization reaction is preferably carried out until the conversion rate of the unsaturated monomer reaches not less than 80%, and more preferably not less than 90%. The upper limit of the conversion rate of the unsaturated monomer is 100%.

The conversion rate of the unsaturated monomer may be determined by nuclear magnetic resonance ($^1$H-NMR) analysis. The detailed procedures of $^1$H-NMR are described below in Examples.

The polymerization reaction time is usually not less than 0.1 h and not more than 60 h, and is preferably not less than 0.5 h, more preferably not less than 1 h, still more preferably not less than 2 h, and even still more preferably not less than 4 h, from the viewpoint of a good operability, and is also preferably not more than 30 h, more preferably not more than 20 h, and still more preferably not more than 10 h, from the viewpoint of a high productivity. During the polymerization reaction, in the case where the raw materials are added dropwise or in split parts, i.e., not at one time but for a certain period of time, the polymerization reaction time includes the time required for addition of the raw materials. The polymerization reaction time can be shortened, for example, by raising the polymerization reaction temperature, and may be suitably adjusted according to the polymerization reaction temperature.

The radical-reactive organopolysiloxane and the unsaturated monomer as the raw materials, the solvent, the polymerization initiator, etc., may be added at one time to conduct the polymerization reaction. Alternatively, in order to control the composition of the resulting product, the polymerization reaction may be carried out by feeding these components in a split addition manner or in a dropwise addition manner. For example, there may be used (1) a method in which the radical-reactive organopolysiloxane, the unsaturated monomer and the solvent are mixed and heated, and then a solution into which the initiator is dissolved is added at one time or dropwise to the resulting mixture; (2) a method in which the solvent is heated, and then the radical-reactive organopolysiloxane, the unsaturated monomer and the initiator are each independently added to the solvent, or a solution prepared by mixing and dissolving these components in the solvent is added dropwise thereto; (3) a method in which the radical-reactive organopolysiloxane, a part of the unsaturated monomer and the solvent are mixed and heated, and then a solution in which the initiator and a remaining part of the unsaturated monomer are dissolved is added at one time or dropwise to the resulting mixture; or the like.

In addition, after completion of the polymerization reaction, the resulting product may be subjected to purification treatments, reduction of the unreacted unsaturated monomer therein or the like by known methods, if required. For example, the amounts of the unreacted unsaturated monomer and other impurities in the product may be reduced by heating after addition of the polymerization initiator thereto, membrane purification, adsorbent treatment, etc.

[Hair Cosmetic]

(Graft Polymer of the Present Invention (Component (A)))

The hair cosmetic used in the present invention contains the graft polymer of the present invention (hereinafter also referred to as a "component (A)"). By incorporating the graft polymer of the present invention into the hair cosmetic, it is possible to attain a soft touch, a hair setting property that is free from change of a hair style even upon combing of hand or fingers through hair, and a more natural finish feeling.

The content of the component (A) in the hair cosmetic is preferably not less than 0.01% by mass, more preferably not less than 0.05% by mass, still more preferably not less than 0.1% by mass, and even still more preferably not less than 0.5% by mass, and is also preferably not more than 50% by mass, more preferably not more than 30% by mass, still more preferably not more than 20% by mass, and even still more preferably not more than 10% by mass, on the basis of a total amount of the hair cosmetic (however, in the case of a spray-type hair cosmetic containing a propellant, a mass of the propellant is excluded from the total amount of the hair cosmetic), from the viewpoints of a good hair setting property of the hair cosmetic of the present invention, a good hair style retentivity thereof after the setting, and a good water dispersibility of the graft polymer of the present invention. By controlling the content of the component (A) in the hair cosmetic to the above-specified range, in particular, when using the below-mentioned organic solvent in combination with an organic acid or a salt thereof, it is possible to further enhance both a hair setting property and a hair style retentivity after hair setting without inhibiting a hair modifying effect by the organic acid and organic solvent (such as enhancement in hair manageability).

(Solvent)

The hair cosmetic of the present invention may also contain, in addition to the above components, at least one solvent selected from the group consisting of water and straight-chain or branched-chain, saturated or unsaturated alcohols having not less than 1 and not more than 3 carbon atoms, from the viewpoints of a hair setting property, a good feeling of use and a good operability upon preparation of the hair cosmetic. Of these solvents, preferred is at least one solvent selected from the group consisting of water, ethanol and isopropanol, and more preferred is at least one solvent selected from the group consisting of water and ethanol.

(Organic Solvent (Component (B)))

The hair cosmetic of the present invention may further contain an organic solvent (hereinafter referred to as a "component (B)") as a preferred component form the viewpoints of attaining an effect of improving bounce and body of hair, an effect of improving softness and manageability of hair, promotion of improving effects (such as resilience improving effect and moisture resistance improving effect), etc., and enhancing a hair setting property by compatibilizing the component (B) with the component (A).

Examples of the organic solvent include butanol, isobutanol, ethylene glycol, propylene glycol, dipropylene glycol, 1,3-butanediol, benzyl alcohol, 2-benzyloxy ethanol, N-methyl pyrrolidone, propylene carbonate, γ-butyrolactone and γ-caprolactone.

(Organic Carboxylic Acid and Salt Thereof (Component (C)))

Also, the hair cosmetic used in the present invention may contain, together with the component (B), an organic carboxylic acid or a salt thereof which may contain a hydroxyl group (hereinafter referred to as a "component (C)") from the viewpoints of attaining an inside modifying effect of hair (such as hollowness mending effect), an effect of improving bounce and body of hair, an effect of improving softness and manageability of hair, and enhancing a hair setting property by compatibilizing the component (C) with the component (A). Examples of the preferred component (C) include lactic acid and malic acid.

(Set Polymer (Component (D)))

Further, the hair cosmetic used in the present invention may contain, in addition to the component (A) as the set polymer, an additional set polymer (hereinafter referred to as a "component (D)"), if required.

Examples of the additional set polymer as the component (D) include vinyl pyrrolidone-based polymers such as Polyvinylpyrrolidone, and acrylate-based polymers such as (meth)acrylic acid/(meth)acrylic acid ester copolymers.

(Conditioning Component)

The hair cosmetic used in the present invention may also contain a conditioning component selected from oil agents and silicones (except for the component (A) of the present invention) for the purpose of further enhancing a conditioning effect of hair.

Examples of the oil agents include hydrocarbons such as squalene, squalane, liquid isoparaffin, light liquid isoparaffin, heavy liquid isoparaffin and α-olefin oligomers; glycerides such as castor oil; waxes such as beeswaxes and carnauba waxes; higher alcohols such as stearyl alcohol; esters such as octyl dodecyl myristate; higher fatty acids such as coconut oil fatty acid; solid fats such as vaseline; and silicones such as dimethyl polysiloxane, polyether-modified silicones and amino-modified silicones (except for the component (A) of the present invention).

(Surfactant)

The hair cosmetic of the present invention may also contain a surfactant from the viewpoints of improving a stability of the system including a solubilizability or a dispersibility of the oil agent, etc., and enhancing a touch feeling. As the surfactant, there may be used any of a cationic surfactant, a nonionic surfactant, an amphoteric surfactant and an anionic surfactant.

Examples of the cationic surfactant include stearyl trimethyl ammonium chloride and behenyl trimethyl ammonium chloride.

Examples of the nonionic surfactant include polyoxyethylene alkyl ethers and polyoxyethylene/polyoxypropylene alkyl ethers.

Examples of the amphoteric surfactant include lauric acid amide propyl betaine, palm kernel oil fatty acid amide propyl betaine and coconut oil fatty acid amide propyl betaine.

Examples of the anionic surfactant include alkyl or alkenyl ether sulfuric acid salts, alkyl or alkenyl sulfuric acid salts, olefin sulfonic acid salts, alkane sulfonic acid salts and saturated or unsaturated fatty acid salts.

(Polyhydric Alcohol)

Further, the hair cosmetic used in the present invention may also contain a polyhydric alcohol other than the component (B). The polyhydric alcohol contributes to solubilization and stable dispersion of the component (B), and also acts synergistically with the component (B) to promote enhancement in hair luster or hair modifying effect. Examples of the polyhydric alcohol include glycerin, sorbitol, etc. Of these polyhydric alcohols, preferred is glycerin.

(Configuration of Hair Cosmetic)

The hair cosmetic used in the present invention may be prepared with various configurations by ordinary methods. Examples of the configurations of the hair cosmetic include not only a liquid composition such as a mist, a lotion and a tonic, but also a semi-solid composition such as a gel, a paste, a cream and a wax.

The hair cosmetic of the present invention may also contain a propellant, and may be used in the form of an aerosol type hair cosmetic. The propellant contained in the hair cosmetic is not particularly limited as long as it can be usually used in the aerosol type hair cosmetic. Examples of the propellant usable in the present invention include lower saturated hydrocarbons such as propane, butane and mixtures thereof (including liquefied petroleum gases); ethers such as dimethyl ether; and a nitrogen gas, a carbon dioxide gas and a nitrous oxide gas. These propellants may be used alone or in combination of any two or more thereof.

The content of the propellant in the hair cosmetic of the present invention is preferably no less than 0.01% by mass, and more preferably not less than 10% by mass, and is also preferably not more than 100% by mass, and more preferably not more than 40% by mass.

Furthermore, the hair cosmetic of the present invention may also be used in the form of a non-aerosol type hair cosmetic by filling a composition containing the organopolysiloxane as the component (A) into a foam injection container. The foam injection container is not particularly limited as long as it is capable of mixing the composition with air and injecting the resulting mixture in a foamed state therefrom. Examples of the foam injection container include a squeeze foamer that is used by pressing a barrel of a soft container with hand or fingers, a pump foamer that is used by pressing a head of a cap equipped with a pump mechanism with hand or fingers, a trigger type foamer, etc.

As the squeeze foamer, there may be mentioned those squeeze foamers described in JUM 62-042785B, JUM 62-042786B and JUM 62-042787B, and similar products thereto. As the pump foamer, there may be mentioned those pump foamers described in JP 7-315463A, JP 08-230961A, etc., and similar products thereto. These containers may be frequently provided at an injection portion thereof with a screen for the purpose of improving a quality of injected foam. Of these containers, preferred are those containers equipped with one or more screens having an opening size of not less than 100 mesh and not more than 300 mesh.

The hair cosmetic is preferably used in the form of a hair styling agent, a hair conditioning agent, etc. Examples of the preferred agent types of the hair cosmetic include a pump spray, an aerosol spray, a pump foam, an aerosol foam, a gel, a lotion, a mist and a cream. Of these agent types, preferred are a pump spray, a pump foam and an aerosol foam.

With respect to the aforementioned embodiments of the present invention, there are further described the following aspects concerning the organopolysiloxane graft polymer as well as the hair cosmetic containing the organopolysiloxane graft polymer.

<1> An organopolysiloxane graft polymer including an organopolysiloxane segment as a main chain thereof and an unsaturated monomer-derived polymer segment as a side chain thereof, in which the unsaturated monomer-derived polymer segment contains a repeating unit derived from N,N-dimethyl acrylamide in an amount of not less than 50% by mass and not more than 100% by mass, and a content of the organopolysiloxane segment in the organopolysiloxane graft polymer is not less than 10% by mass and not more than 70% by mass.

<2> The organopolysiloxane graft polymer according to the above aspect <1>, wherein a content of the organopolysiloxane segment in the organopolysiloxane graft polymer is not less than 20% by mass, and more preferably not less than 30% by mass, and is also not more than 60% by mass, and preferably not more than 50% by mass.

<3> The organopolysiloxane graft polymer according to the above aspect <1> or <2>, wherein a weight-average molecular weight (MWsi) of the organopolysiloxane segment is not less than 3,000, preferably not less than 5,000, more preferably not less than 10,000, and still more preferably not less than 15,000, and is also not more than 200,000, preferably not more than 100,000, more preferably not more than 60,000, and still more preferably not more than 50,000.

<4> The organopolysiloxane graft polymer according to any one of the above aspects <1> to <3>, wherein a number-average molecular weight (MNg) of the organopolysiloxane segment being present between the adjacent unsaturated monomer-derived polymer segments is not less than 500, preferably not less than 700, more preferably not less than 1,000, and still more preferably not less than 1,500, and is also not more than 10,000, preferably not more than 5,000, more preferably not more than 3,000, and still more preferably not more than 2,500.

<5> The organopolysiloxane graft polymer according to any one of the above aspects <1> to <4>, wherein a mass ratio (a/b) of the organopolysiloxane segment (a) to the unsaturated monomer-derived polymer segment (b) is not less than 10/90, preferably not less than 20/80, more preferably not less than 30/70, and still more preferably not less than 35/65, and is also not more than 70/30, preferably not more than 60/40, and more preferably not more than 50/50.

<6> The organopolysiloxane graft polymer according to any one of the above aspects <1> to <5>, wherein a weight-average molecular weight (MWt) of the organopolysiloxane graft polymer is not less than 10,000, preferably not less than 14,000, more preferably not less than 17,000, and still more preferably not less than 30,000, and is also not more than 200,000, preferably not more than 160,000, more preferably not more than 130,000, and still more preferably not more than 95,000.

<7> The organopolysiloxane graft polymer according to any one of the above aspects <1> to <6>, wherein the unsaturated monomer-derived polymer segment further includes a repeating unit derived from at least one unsaturated monomer selected from the group consisting of (meth)acrylamides except for N,N-dimethyl acrylamide and (meth)acrylates; preferably a repeating unit derived from at least one unsaturated monomer selected from the group consisting of acrylamide, methacrylamide, N,N-diethyl (meth)acrylamide, N-isopropyl (meth)acrylamide, N-tert-butyl (meth)acrylamide, diacetone (meth)acrylamide, N,N-dimethylaminopropyl (meth)acrylamide, N-hydroxyethyl (meth)acrylamide, N-methylol (meth)acrylamide, methyl (meth)acrylate, ethyl (meth)acrylate, propyl (meth)acrylate, isobutyl (meth)acrylate, n-butyl (meth)acrylate, tert-butyl (meth)acrylate and 2-hydroxyethyl (meth)acrylate; more preferably a repeating unit derived from at least one unsaturated monomer selected from the group consisting of N-tert-butyl (meth)acrylamide, N-hydroxyethyl (meth)acrylamide, diacetone (meth)acrylamide, methyl (meth)acrylate, ethyl (meth)acrylate, tert-butyl (meth)acrylate and N,N-dimethylaminopropyl (meth)acrylamide; still more preferably a repeating unit derived from at least one unsaturated monomer selected from the group consisting of N-tert-butyl (meth)acrylamide, N-hydroxyethyl (meth)acrylamide, diacetone (meth)acrylamide, methyl (meth)acrylate, ethyl (meth)acrylate and tert-butyl (meth)acrylate; and even still more preferably N-tert-butyl (meth)acrylamide.

<8> The organopolysiloxane graft polymer according to any one of the above aspects <1> to <7>, wherein the organopolysiloxane segment is a modified organopolysiloxane segment represented by the following general formula (1) or (2):

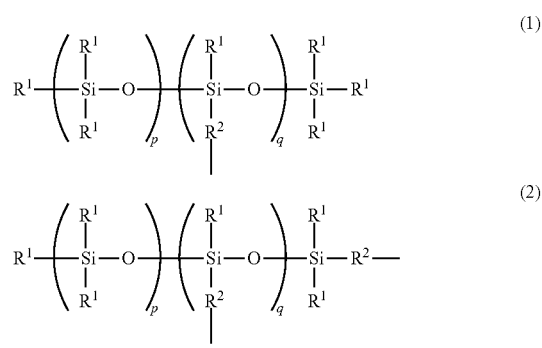

wherein $R^1$ groups are each independently an alkyl group having not less than 1 and not more than 22 carbon atoms or an aryl group having not less than 6 and not more than 14 carbon atoms; $R^2$ groups are each an alkylene group that may contain a hetero atom; p is a number of not less than 2 and not more than 4,000; q is a number of not less than 2 and not more than 250; and in the above general formulae (1) and (2), the repeating units in the number of p and the repeating units in the number of q may be bonded to each other either in a block form or in a random form.

<9> The organopolysiloxane graft polymer according to the above aspect <8>, wherein in the above general formulae (1) and (2), $R^1$ is a straight-chain or branched-chain alkyl group having not less than 1 and not more than 6 carbon atoms, preferably a straight-chain or branched-chain alkyl group having not less than 1 and not more than 3 carbon atoms, and more preferably a methyl group.

<11> The organopolysiloxane graft polymer according to the above aspect <8> or <9>, wherein in the above general formulae (1) and (2), p is a number of not less than 2, preferably not less than 50, more preferably not less than 80, and still more preferably not less than 100, and is also a number of not more than 4,000, preferably not more than 2,000, more preferably not more than 1,300, and still more preferably not more than 700.

<11> The organopolysiloxane graft polymer according to any one of the above aspects <8> to <10>, wherein in the above general formulae (1) and (2), q is a number of not less than 2, preferably not less than 3, and more preferably not less than 5, and is also a number of not more than 250, preferably not more than 50, and more preferably not more than 30.

<12> The organopolysiloxane graft polymer according to any one of the above aspects <8> to <11>, wherein in the above general formulae (1) and (2), the number of carbon atoms of the alkylene group ($R^2$) which may contain a hetero atom is not less than 2, and preferably not less than 3, and is also not more than 20, preferably not more than 10, and more preferably not more than 8.

<13> The organopolysiloxane graft polymer according to any one of the above aspect <8> to <12>, wherein in the above general formulae (1) and (2), the alkylene group ($R^2$) which may contain a hetero atom is bonded to the unsaturated monomer-derived polymer segment through the hetero atom, preferably through a nitrogen atom, an oxygen atom or a sulfur atom, and more preferably through a sulfur atom.

<14> The organopolysiloxane graft polymer according to any one of the above aspects <8> to <13>, wherein in the above general formulae (1) and (2), the alkylene group ($R^2$) which may contain a hetero atom is a group selected from the group consisting of those groups represented by the following formulae (i) to (xii), and preferably a group selected from the group consisting of those groups represented by the following formulae (xi) and (xii):

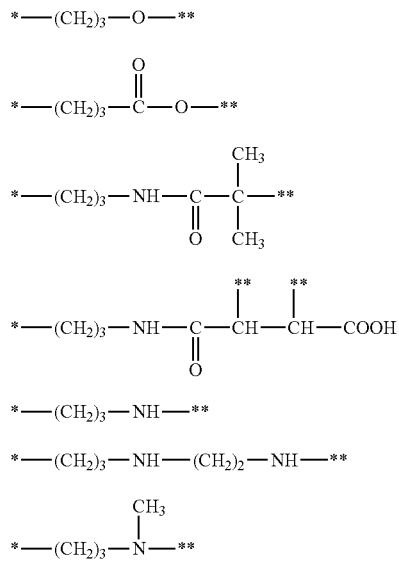

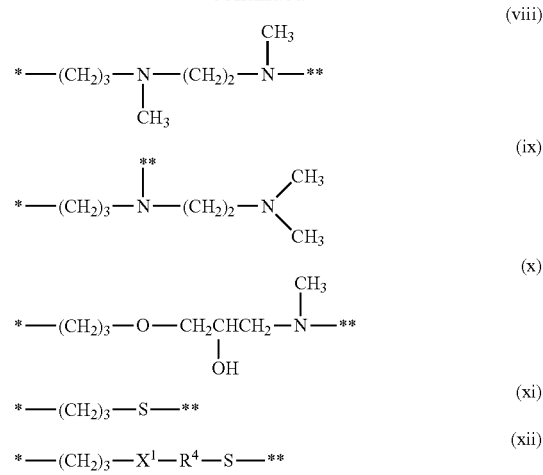

wherein "*" represents a moiety bonded to the silicon atom in the general formula (1) or (2), and "**" represents a moiety bonded to the unsaturated monomer-derived polymer segment;

in the formula (xii), $X^1$ is an atom or group selected from the group consisting of —O—, —OCO—, —COO—, —CONH—, and —NHCO—; and in the formula (xii), $R^4$ is an alkylene group that may be substituted with at least one substituent group selected from the group consisting of a hydroxyl group, an amino group, a ($C_1$-$C_3$) alkyl amino group, a di-($C_1$-$C_3$) alkyl amino group, an amide group obtained by dehydration condensation of an amino group and a fatty acid having not less than 2 and not more than 4 carbon atoms, and a ($C_1$-$C_3$) alkyl ester group.

<15> The organopolysiloxane graft polymer according to the above aspect <14>, wherein in the formula (xii), $X^1$ is —CONH— or —NHCO—, and preferably —NHCO—.

<16> The organopolysiloxane graft polymer according to the above aspect <14> or <15>, wherein in the formula (xii), $R^4$ is an alkylene group that is substituted with an acetamide group, a ($C_1$-$C_3$) alkyl amino group or an amino group.

<17> The organopolysiloxane graft polymer according to the above aspect <14>, wherein in the formula (xii), $R^4$ is a group selected from the group consisting of those groups represented by the following formulae (xiii) to (xv):

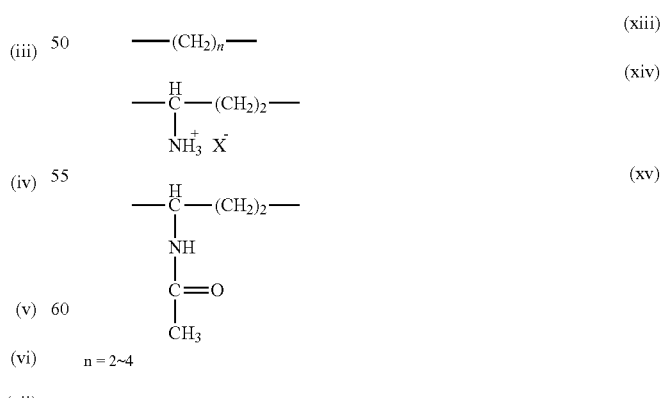

n = 2~4 wherein $X^-$ in the formula (xiv) is an anion.

<18> The organopolysiloxane graft polymer according to any one of the above aspects <1> to <17>, wherein a content of the repeating unit derived from N,N-dimethyl acrylamide in the unsaturated monomer-derived polymer segment is not less than 70% by mass, and preferably not less than 75% by mass, and is also not more than 95% by mass, and preferably not more than 90% by mass.

<19> The organopolysiloxane graft polymer according to any one of the above aspects <1> to <18>, wherein the organopolysiloxane graft polymer is produced by subjecting an unsaturated monomer to polymerization in the presence of a radical-reactive organopolysiloxane represented by the following general formula (4) or (5).

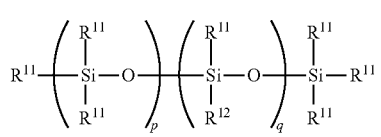
(4)

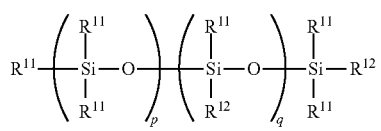
(5)

wherein $R^{11}$ groups are each independently an alkyl group having not less than 1 and not more than 22 carbon atoms or an aryl group having not less than 6 and not more than 14 carbon atoms; $R^{12}$ groups are each an alkyl group containing a radical-reactive functional group; p is a number of not less than 2 and not more than 4,000; q is a number of not less than 2 and not more than 250; and in the above general formulae (4) and (5), the repeating units in the number of p and the repeating units in the number of q may be bonded to each other either in a block form or in a random form.

<20> The organopolysiloxane graft polymer according to the above aspect <19>, wherein in the above general formulae (4) and (5), $R^{11}$ is a straight-chain or branched-chain alkyl group having not less than 1 and not more than 6 carbon atoms, preferably a straight-chain or branched-chain alkyl group having not less than 1 and not more than 3 carbon atoms, and more preferably a methyl group.

<21> The organopolysiloxane graft polymer according to the above aspect <19> or <20>, wherein in the general formulae (4) and (5), p is a number of not less than 2, preferably not less than 50, more preferably not less than 80, and still more preferably not less than 100, and is also a number of not more than 4,000, preferably not more than 2,000, more preferably not more than 1,300, and still more preferably not more than 700.

<22> The organopolysiloxane graft polymer according to any one of the above aspects <19> to <21>, wherein in the general formulae (4) and (5), q is a number of not less than 2, preferably not less than 3, and more preferably not less than 5, and is also a number of not more than 250, preferably not more than 50, and more preferably not more than 30.

<23> The organopolysiloxane graft polymer according to any one of the above aspects <19> to <22>, wherein the radical-reactive functional group is a group selected from the group consisting of an ethylenically unsaturated group, a halogeno group and a sulfanyl group, and preferably a sulfanyl group.

<24> The organopolysiloxane graft polymer according to any one of the above aspects <19> to <23>, wherein in the general formulae (4) and (5), the number of carbon atoms of the radical-reactive group-containing alkyl group represented by $R^{12}$ is not less than 2, and preferably not less than 3, and is also not more than 20, preferably not more than 10, and more preferably not more than 8.

<25> The organopolysiloxane graft polymer according to any one of the above aspects <19> to <24>, wherein in the general formulae (4) and (5), the radical-reactive group-containing alkyl group represented by $R^{12}$ is substituted with at least one substituent group selected from the group consisting of a hydroxyl group, an amino group, a $(C_1\text{-}C_3)$ alkyl amino group, a di-$(C_1\text{-}C_3)$ alkyl amino group, an amide group obtained by dehydration condensation of an amino group and a fatty acid having not less than 2 and not more than 4 carbon atoms, a carboxyl group, and a $(C_1\text{-}C_3)$ alkyl ester group, and preferably an acetamide group, a $(C_1\text{-}C_3)$ alkyl amino group or an amino group.

<26> The organopolysiloxane graft polymer according to any one of the above aspects <19> to <25>, wherein in the general formulae (4) and (5), the radical-reactive group-containing alkyl group represented by $R^{12}$ is interrupted by at least one atom or functional group selected from the group consisting of an oxygen atom, a sulfur atom, —NH—, —COO—, —NHCO— and —NR$^{13}$CO—, and preferably by —NHCO—, in which $R^{13}$ is an alkyl group having not less than 1 and not more than 3 carbon atoms.

<27> The organopolysiloxane graft polymer according to any one of the above aspects <19> to <26>, wherein in the general formulae (4) and (5), the radical-reactive group-containing alkyl group represented by $R^{12}$ is a group selected from the group consisting of those groups represented by the following formulae (xvii) to (xx), and preferably a group represented by the following formula (xix) or (xx):

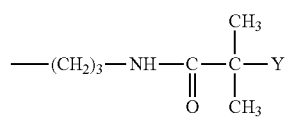
(xvii)

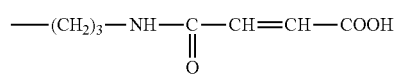
(xviii)

(xix)

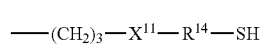
(xx)

Y = Cl or Br wherein $X^{11}$ in the formula (xx) is an atom or group selected from the group consisting of —O—, —OCO—, —COO—, —CONH—, and —NHCO—; and $R^{14}$ in the formula (xx) is an alkylene group that may be substituted with at least one substituent group selected from the group consisting of a hydroxyl group, an amino group, a $(C_1\text{-}C_3)$ alkyl amino group, a di-$(C_1\text{-}C_3)$ alkyl amino group, an amide group obtained by dehydration condensation of an amino group and a fatty acid having not less than 2 and not more than 4 carbon atoms, and a $(C_1\text{-}C_3)$ alkyl ester group, and preferably an alkylene group that is substituted with an acetamide group, a $(C_1\text{-}C_3)$ alkyl amino group or an amino group.

<28> The organopolysiloxane graft polymer according to the above aspect <27>, wherein in the formula (xx), $X^{11}$ is —CONH— or —NHCO—, and preferably —NHCO—.

<29> The organopolysiloxane graft polymer according to the above aspect <27> or <28>, wherein in the formula (xx), $R^{14}$ is an alkylene group that is substituted with an acetamide group, a $(C_1\text{-}C_3)$ alkyl amino group or an amino group.

<30> The organopolysiloxane graft polymer according to any one of the above aspects <19> to <29>, wherein a weight-average molecular weight (MWra) of the radical-reactive organopolysiloxane is not less than 3,000, preferably not less than 5,000, more preferably not less than 10,000, and still more preferably not less than 15,000, and is also not more than 200,000, preferably not more than 100,000, more preferably not more than 60,000, and still more preferably not more than 50,000.

<31> The organopolysiloxane graft polymer according to any one of the above aspects <19> to <30>, wherein the number of moles of the radical-reactive functional group being present per a unit mass of the radical-reactive organopolysiloxane is not more than 1/500 mol/g, preferably not more than 1/700 mol/g, and more preferably not more than 1/1,000 mol/g, and is also not less than 1/10,000 mol/g, preferably not less than 1/5,000 mol/g, and more preferably not less than 1/3,000 mol/g.

<32> The organopolysiloxane graft polymer according to any one of the above aspects <19> to <31>, wherein an amount of the unsaturated monomer used is not less than 30% by mass, preferably not less than 40% by mass, and more preferably not less than 50% by mass, and is also not more than 90% by mass, preferably not more than 80% by mass, and more preferably not more than 70% by mass, on the basis of a total amount of the radical-reactive organopolysiloxane and the unsaturated monomer.

<33> The organopolysiloxane graft polymer according to any one of the above aspects <19> to <32>, wherein a content of N,N-dimethyl acrylamide in the unsaturated monomer is not less than 50% by mass, preferably not less than 70% by mass, and more preferably not less than 75% by mass, and is also not more than 100% by mass, preferably not more than 95% by mass, and more preferably not more than 90% by mass.

<34> The organopolysiloxane graft polymer according to any one of the above aspects <19> to <33>, wherein the unsaturated monomer is an unsaturated monomer (except for DMVAAm) capable of copolymerizing with DMAAm; preferably at least one unsaturated monomer selected from the group consisting of (meth)acrylamides except for N,N-dimethyl acrylamide and (meth)acrylates; more preferably at least one unsaturated monomer selected from the group consisting of acrylamide, methacrylamide, N,N-diethyl (meth)acrylamide, N-isopropyl (meth)acrylamide, N-tert-butyl (meth)acrylamide, diacetone (meth)acrylamide, N,N-dimethylaminopropyl (meth)acrylamide, N-hydroxyethyl (meth)acrylamide, N-methylol (meth)acrylamide, methyl (meth)acrylate, ethyl (meth)acrylate, propyl (meth)acrylate, isobutyl (meth)acrylate, n-butyl (meth)acrylate, tert-butyl (meth)acrylate and 2-hydroxyethyl (meth)acrylate; still more preferably at least one unsaturated monomer selected from the group consisting of N-tert-butyl (meth)acrylamide, N-hydroxyethyl (meth)acrylamide, diacetone (meth)acrylamide, methyl (meth)acrylate, ethyl (meth)acrylate, tert-butyl (meth)acrylate and N,N-dimethylaminopropyl (meth) acrylamide; and even still more preferably at least one unsaturated monomer selected from the group consisting of N-tert-butyl (meth)acrylamide, N-hydroxyethyl (meth)acrylamide, diacetone (meth)acrylamide, methyl (meth)acrylate, ethyl (meth)acrylate and tert-butyl (meth)acrylate.

<35> The organopolysiloxane graft polymer according to any one of the above aspects <19> to <34>, wherein the polymerization is carried out by solution polymerization in the presence of a solvent.

<36> The organopolysiloxane graft polymer according to any one of the above aspects <19> to <35>, wherein the solvent is at least one solvent selected from the group consisting of alcohols having not less than 1 and not more than 8 carbon atoms, esters having not less than 2 and not more than 8 carbon atoms, and ethers having not less than 2 and not more than 8 carbon atoms, and preferably at least one solvent selected from the group consisting of water and alcohols having not less than 1 and not more than 3 carbon atoms.

<37> The organopolysiloxane graft polymer according to any one of the above aspects <19> to <36>, wherein an amount of the solvent used is not less than 20% by mass, preferably not less than 40% by mass, more preferably not less than 60% by mass, and still more preferably not less than 100% by mass, and is also not more than 1,000% by mass, preferably not more than 900% by mass, more preferably not more than 400% by mass, and still more preferably not more than 300% by mass, on the basis of a total amount of the radical-reactive organopolysiloxane and the unsaturated monomer.

<38> The organopolysiloxane graft polymer according to any one of the above aspects <19> to <37>, wherein the polymerization is carried out in the presence of a polymerization initiator, preferably a polymerization initiator selected from the group consisting of an azo-based initiator, a peroxide-based initiator and a persulfate-based initiator, more preferably a polymerization initiator selected from the group consisting of 2,2'-azobisisobutyronitrile, 2,2'-azobis (2,4-dimethyl valeronitrile), lauroyl peroxide, benzoyl peroxide and ammonium persulfate, and still more preferably 2,2'-azobis(2,4-dimethyl valeronitrile).

<39> The organopolysiloxane graft polymer according to the above aspect <38>, wherein an amount of the polymerization initiator used is not less than 0.001% by mass, and preferably not less than 0.01% by mass, and is also not more than 10% by mass, and preferably not more than 1% by mass, on the basis of a total amount of the unsaturated monomer used.

<40> The organopolysiloxane graft polymer according to any one of the above aspects <19> to <39>, wherein a temperature at which the polymerization is carried out is not lower than 50° C., and preferably not lower than 60° C., and is also not higher than 100° C., and preferably no higher than 90° C.

<41> The organopolysiloxane graft polymer according to any one of the above aspects <19> to <40>, wherein the polymerization is carried out until a conversion rate of the unsaturated monomer reaches not less than 80%, and preferably not less than 90% and not more than 100%.

<42> The organopolysiloxane graft polymer according to any one of the above aspects <19> to <41>, wherein a time of the polymerization is not less than 0.1 h, preferably not less than 0.5 h, more preferably not less than 1 h, still more preferably not less than 2 h, and even still more preferably not less than 4 h, and is also not more than 60 h, preferably not more than 30 h, more preferably not more than 20 h, and still more preferably not more than 10 h.

<43> The organopolysiloxane graft polymer according to any one of the above aspects <19> to <42>, wherein the radical-reactive organopolysiloxane is produced by reacting a reactive functional group-containing organopolysiloxane represented by the following general formula (6) or (7) with a radical reactivity-imparting agent:

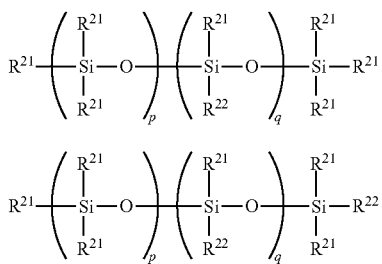

(6)

(7)

wherein $R^{21}$ groups are each independently an alkyl group having not less than 1 and not more than 22 carbon atoms or an aryl group having not less than 6 and not more than 14 carbon atoms; $R^{22}$ groups are each an alkyl group containing a reactive functional group; p is a number of not less than 2 and not more than 4,000; q is a number of not less than 2 and not more than 250; and in the above general formulae (6) and (7), the repeating units in the number of p and the repeating units in the number of q may be bonded to each other either in a block form or in a random form.

<44> The organopolysiloxane graft polymer according to the above aspect <43>, wherein the reactive functional group is a group selected from the group consisting of a hydroxyl group, an amino group, a carboxyl group and an epoxy group.

<45> The organopolysiloxane graft polymer according to the above aspect <43> or <44>, wherein in the general formulae (6) and (7), the number of carbon atoms of the reactive group-containing alkyl group represented by $R^{22}$ is not less than 2, and preferably not less than 3, and is also not more than 15, preferably not more than 10, and more preferably not more than 5.

<46> The organopolysiloxane graft polymer according to any one of the above aspects <43> to <45>, wherein in the general formulae (6) and (7), the reactive group-containing alkyl group represented by $R^{22}$ is a group selected from the group consisting of those groups represented by the following formulae (xxi) to (xxviii), preferably a group selected from the group consisting of those groups represented by the following formulae (xxi) to (xxiv), and more preferably a group represented by the following formula (xxiv).

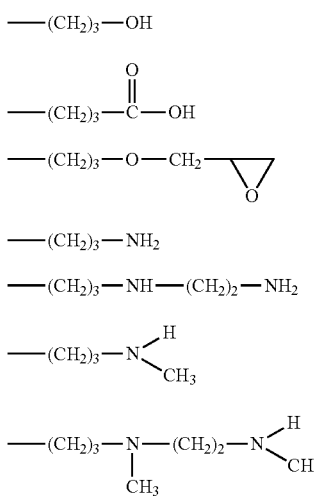

(xxi)
(xxii)
(xxiii)
(xxiv)
(xxv)
(xxvi)
(xxvii)

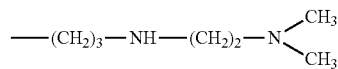

(xxviii)

<47> The organopolysiloxane graft polymer according to any one of the above aspects <43> to <46>, wherein a weight-average molecular weight (MWsim) of the reactive functional group-containing organopolysiloxane is not less than 3,000, preferably not less than 5,000, more preferably not less than 10,000, and still more preferably not less than 15,000, and is also not more than 200,000, preferably not more than 100,000, more preferably not more than 60,000, and still more preferably not more than 50,000.

<48> The organopolysiloxane graft polymer according to any one of the above aspects <43> to <47>, wherein the number of moles of the reactive functional group being present per a unit mass of the reactive functional group-containing organopolysiloxane is not more than 1/500 mol/g, preferably not more than 1/700 mol/g, and more preferably not more than 1/1,000 mol/g, and is also not less than 1/10,000 mol/g, preferably not less than 1/5,000 mol/g, and more preferably not less than 1/3,000 mol/g.

<49> The organopolysiloxane graft polymer according to any one of the above aspects <43> to <48>, wherein the radical reactivity-imparting agent is a compound containing a radical-reactive functional group and at least one functional group capable of reacting with the reactive functional group of the reactive functional group-containing organopolysiloxane which is selected from the group consisting of a carboxyl group, an ester group, an epoxy group, a hydroxyl group and a lactone, in a molecule thereof, or an unsubstituted or substituted thiolactone.

<50> The organopolysiloxane graft polymer according to the above aspect <49>, wherein the radical-reactive functional group of the radical reactivity-imparting agent is a group selected from the group consisting of an ethylenically unsaturated group, a halogeno group and a sulfanyl group, and preferably a sulfanyl group.

<51> The organopolysiloxane graft polymer according to any one of the above aspects <43> to <49>, wherein the radical reactivity-imparting agent is at least one compound selected from the group consisting of 3-mercapto propionic acid, γ-butyrolactone thiol, γ-thiobutyrolactone, N-acetyl-DL-homocysteine thiolactone and DL-homocysteine thiolactone hydrochloride, and preferably N-acetyl-DL-homocysteine thiolactone.

<52> The organopolysiloxane graft polymer according to any one of the above aspects <43> to <51>, wherein an amount of the radical reactivity-imparting agent used is not less than 0.8 equivalent, and preferably not less than 0.9 equivalent, and is also not more than 1.2 equivalent, and preferably not more than 1.1 equivalent, on the basis of a total amount of the reactive functional group of the reactive functional group-containing organopolysiloxane.

<53> A hair cosmetic including the organopolysiloxane graft polymer according to any one of the above aspects <1> to <52>.

EXAMPLES

<GPC Measuring Conditions of Weight-Average Molecular Weights (MWsim, MWra and MWt) of Reactive Functional Group-Containing Organopolysiloxane, Radical-Reactive Organopolysiloxane and Organopolysiloxane Graft Polymer)

Column: "K-804L" (available from Tosoh Corp.); Two columns connected in series were used.

Eluent: 1 mM Dimethyl dodecyl amine/chloroform solution

Flow Rate: 1.0 mL/min

Column Temperature: 40° C.

Detector: RI

Concentration and Amount of Sample: 5 mg/mL; 500 μL

Under the above measuring conditions, the weight-average molecular weight of each of the reactive functional group-containing organopolysiloxane, the radical-reactive organopolysiloxane and the organopolysiloxane graft polymer was measured in terms of a polystyrene as a reference standard substance.

<Calculation of Number of Moles of Sulfanyl Group Per Unit Mass of Sulfanyl Group-Modified Organopolysiloxane (Radical-Reactive Organopolysiloxane) Synthesized from Side-Chain Primary Aminopropyl-Modified Organopolysiloxane (Reactive Functional Group-Containing Organopolysiloxane)>

The amount of an amino group contained in a mixture of a side-chain primary aminopropyl-modified organopolysiloxane (reactive functional group-containing organopolysiloxane) and a sulfanyl group-modified organopolysiloxane (radical-reactive organopolysiloxane) obtained by the reaction between the side-chain primary aminopropyl-modified organopolysiloxane and N-acetyl-DL-homocysteine thiolactone (radical reactivity-imparting agent) was measured to determine an amount of the amino group consumed by the reaction. The measurement of the amount of the amino group was carried out according to ASTM D 2073. More specifically, about 10 g of a sample (radical-reactive organopolysiloxane) was weighed and sampled in a flask, and 50 mL of ethanol was added thereto, followed by stirring the contents of the flask. Using a potentiometric titration apparatus, the resulting reaction solution was subjected to titration with a 0.2 mol/L ethanolic hydrochloric acid solution. At the same time, a blank test of the above measurement was conducted to correct the above measured value.

From the amount of the amino group thus measured, a conversion rate α (%) of the amino group was first determined from the following formula (IV):

$$\alpha(\%) = [1 - [a_1 \times (f+g)/(a_0 \times f)]] \times 100 \quad (IV).$$

In the above formula (IV), $a_0$ and $a_1$ are the number of moles of the amino group per a unit mass of the side-chain primary aminopropyl-modified organopolysiloxane and the number of moles of the amino group per a unit mass of a reaction mixture obtained after the reaction thereof with the radical reactivity-imparting agent, respectively; f is a total amount of the side-chain primary aminopropyl-modified organopolysiloxane charged; and g is a total amount of the radical reactivity-imparting agent charged.

Assuming that the radical-reactive organopolysiloxane obtained after the reaction had the same number of sulfanyl groups produced thereon as that of amino groups consumed by the reaction, the number of moles (S) of the sulfanyl group per a unit mass of the sulfanyl group-modified organopolysiloxane was calculated from the following calculation formula (V):

$$S \text{ (mol/g)} = (a_0 \times f \times \alpha/100)/[f + (a_0 \times f \times \alpha/100) \times h] \quad (V).$$

In the above formula (V), $a_0$, f and a are the same as $a_0$, f and a as defined the above formula (IV); and h is a molecular weight of the radical reactivity-imparting agent.

<Method of Measuring Residual Rate of Sulfanyl Group (Mercapto Group)>

A 10 mL screw bottle was charged with 0.6 g of a 50% by mass ethanol solution of the organopolysiloxane graft polymer, 0.15 g of a 10% by mass ethanol solution of N-methyl maleimide (available from Sigma-Aldrich Co.) and 0.55 g of ethanol, and the contents of the tube were stirred at room temperature for 2 h. After completion of the stirring, 1 g of ethanol was added to the tube, and the obtained reaction solution was analyzed by gas chromatography to quantitatively determine an amount of N-methyl maleimide therein. The residual amount of the sulfanyl group in the resulting product was calculated from a consumption rate of N-methyl maleimide, and further the residual rate of the sulfanyl group in the resulting product was calculated from the thus calculated residual amount value and the number of moles of the sulfanyl group per a unit mass of the sulfanyl group-modified organopolysiloxane.

<Calculation of Molecular Weight Between Graft Points of Organopolysiloxane Graft Polymer>

Assuming that elimination of the sulfanyl group after the polymerization was caused by bonding the unsaturated monomer-derived polymer thereto, the molecular weight between graft points of the organopolysiloxane graft polymer was calculated from the number of moles of the sulfanyl group per a unit mass of the sulfanyl group-modified organopolysiloxane used as the raw material and the residual rate of the sulfanyl group as measured in the above <Method of Measuring Residual Rate of Sulfanyl Group>.

<Method of Measuring Content of Unsaturated Monomer-Derived Polymer Unbonded to Organopolysiloxane Graft Polymer in Mixture Containing Organopolysiloxane Graft Polymer Obtained after Completion of Reaction>

In the case of using a graft-from method in which an unsaturated monomer was subjected to radical polymerization in the presence of the radical-reactive organopolysiloxane, an unsaturated monomer-derived polymer that was unbonded to the organopolysiloxane graft polymer was produced in addition to the organopolysiloxane graft polymer. After completion of the polymerization reaction, the content (% by mass) of the unsaturated monomer-derived polymer in the mixture containing the organopolysiloxane graft polymer obtained after removing the solvent therefrom was measured by liquid chromatography. The measuring conditions are shown below.

[Measuring Conditions of Liquid Chromatography]

Detector: UV absorptiometer (measuring wavelength: 230 nm)

Column: ODS Column "L-column ODS" (available from a general incorporated foundation "Chemicals Evaluation and Research Institute, Japan"; size: 4.6×150 mm, 5 μm)

Column Temperature: Constant temperature near 30° C.

Mobile Phase A: 2% Phosphoric acid aqueous solution; Mobile Phase B: 2% Phosphoric acid ethanol solution Flow Rate: 0.5 mL/min Concentration and Amount of Sample: 1 to 2 mg/mL; 10.0 μL <Method of Measuring Mass Ratio (a/b) of Organopolysiloxane Segment (a) to Unsaturated Monomer-Derived Polymer Segment (b) in Organopolysiloxane Graft Polymer by Nuclear Magnetic Resonance (1H-NMR) Analysis>

The organopolysiloxane graft polymer was dissolved in an amount of 5% by mass in deuterated chloroform, and the resulting solution was subjected to $^1$H-NMR measurement using a nuclear magnetic resonance ($^1$H-NMR) apparatus "Mercury 400" (available from Varian Inc.) under the following measuring conditions:

Measuring Mode: Proton 1D; Measuring Temperature: room temperature; Cumulative Frequency: 8 times.

The mass ratio (a/b) was determined from a ratio between an integrated value of a methyl group bonded to a silicon atom in the organopolysiloxane segment (0 ppm) and an integrated value of an alkyl group in the unsaturated monomer-derived polymer segment (a methyl group of N,N-dimethyl acrylamide: near 2.7 to 3.2 ppm; a tert-butyl group of N-tert-butyl acrylamide: 1.0 to 1.4 ppm).

[Evaluation]

<Evaluation of Water Dispersibility>

An aqueous solution or dispersion containing 2.5% by mass of the respective samples, 7.5% by mass of ethanol and 90% by mass of ion-exchanged water was prepared, and a transmittance (T %) of the resulting liquid was measured the following conditions. When the measured transmittance was not less than 70%, it was determined that the sample had a high dispersibility in an aqueous solvent and therefore a high water dispersibility.

Apparatus: UV visible spectrophotometer "UV-2550" (available from Shimadzu Corp.)

Measuring Mode: Transmittance

Measuring Wavelength: 660 nm

Sample: Ethanol/ion-exchanged water aqueous solution or dispersion having a sample concentration of 2.5% by mass Optical Path Length: 1 cm Measuring Temperature: 25° C.

<Measurement of Elastic Modulus>

Measuring Apparatus: Dynamic viscoelasticity measuring apparatus "DVA-225" (available from I.T. Keisoku Seigyo K.K.)

Measuring Mode: Shearing mode

Distortion: 0.01 to 0.1%

Frequency: 1 Hz

Size of Sample: (0.6 to 1.5)×(7 to 10)×(5 to 6) mm

Measuring Temperature Range: −10 to 200° C.

The temperature upon the measurement was allowed to vary within the above measuring temperature range. In order to use the measured value as an index for a setting property of hair with a hair iron or dryer, a storage elastic modulus at 150° C. as a high-temperature elastic modulus was measured as an index for easiness of deformation of a hair style upon setting the hair with the hair iron or dryer, and a storage elastic modulus at 25° C. as a room temperature elastic modulus was measured as an index for a setting property of the hair when returned to room temperature.

(Method of Forming Film)

An adequate amount of an ethanol solution (50% by mass) of the organopolysiloxane graft polymer was placed in a petri dish made of polytetrafluoroethylene, and dried at room temperature (25° C.) for 5 days under a nitrogen flow. Thereafter, the thus dried polymer was further subjected to drying under reduced pressure (20 kPa) at 80° C. for 8 h, thereby obtaining a light-yellow transparent film having a thickness of about 1 mm. The thus obtained film was cut into a film piece, and the cut film piece was used as a test specimen.

<Evaluation of Hair Setting Property>

A 5% by mass ethanol solution of each of the organopolysiloxane graft polymers obtained in the respective Examples and Comparative Examples was prepared, and the thus prepared solution was applied onto hair and dried to evaluate a hair setting property thereof.

(Evaluation Conditions)

A hair bundle of Caucasian curly or kinky hair having a length of 30 cm and a weight of 6 g was used for the evaluation. The hair bundle was wetted with water to moisten a whole portion thereof, and 1.2 g of the 5% by mass ethanol solution of the sample was applied thereonto, and then the hair bundle was combed 5 times on each of front and rear sides thereof. Next, the hair bundle was completely dried using a dryer, and stretched 3 times by a straightening iron and then 2 times by combing. After completing a series of the above treatments, the sensory evaluation was conducted according to the following ratings. The evaluation of each of the items was conducted 5 times in total by three expert panelists to obtain an average value thereof.

(Evaluation Criteria)

(1) Finish of Hair Style (Setting Property)

Under the above treating conditions for the hair bundle, the condition of the hair bundle after treated with the iron was observed by naked eyes and evaluated according the following ratings. When the average evaluation value was 4.0 or more, the finish of hair style was regarded as being good.

5: Curl or kink of hair was stretched straight, and an entire portion of the hair bundle was collected like one plate.

4: Curl or kink of hair was stretched straight, and substantially an entire portion of the hair bundle was collected together.

3: Curl or kink of hair was stretched straight, but the hair bundle was collected weakly.

2: Curl or kink of hair was stretched straight, but the hair bundle was not collected at all.

1: Curl or kink of hair was not stretched.

(2) Touch Feeling (Less Stickiness)

Under the above hair treating conditions, a touch feeling (less stickiness) of hair upon drying the hair using a dryer was evaluated by a sensory test according the following ratings. When the average evaluation value was 3.0 or more, the touch feeling of the hair was regarded as being good.

5: No feeling of stickiness was present.

4: Slight feeling of stickiness was present upon drying, but the feeling of stickiness was soon eliminated.

3: Feeling of stickiness was present upon drying, but the feeling of stickiness was eliminated within 10 s after completion of the drying.

2: Feeling of stickiness was present upon drying, and the feeling of stickiness still remained even when 10 s elapsed after completion of the drying.

1: Feeling of stickiness was continuously present after drying.

(3) Hair Style Retentivity after Setting of Hair Style

The hair bundle after completing a series of the treatments under the above hair treating conditions was suspended such that hair tips thereof faced downwards, and allowed to stand in this state under environmental conditions of a temperature of 25° C. and a relative humidity of 90% or more. After allowing the hair bundle to stand under the above conditions for 1 h, the condition of the hair bundle was observed and evaluated by naked eyes. When the average evaluation value was 3.0 or more, the hair style retentivity was regarded as being good.

5: The hair bundle was collected as a whole, and curl or kink of the hair was keptin a stretched state.

4: The hair bundle was collected as a whole, but hair tips thereof were undulated.

3: The hair bundle was almost collected as a whole, but an entire portion thereof suffered from undulation.

2: The hair bundle was collected weakly, and suffered from remarkable undulation.

1: The hair bundle was not collected but dispersed.

Synthesis Example 1

(Synthesis of Radical-Reactive Organopolysiloxane A)

A separable flask equipped with a reflux condenser, a thermometer, a nitrogen inlet tube and a stirrer was charged with 100 g of a side-chain primary aminopropyl-modified organopolysiloxane (weight-average molecular weight: 30,000; number of moles of an amino group per a unit mass thereof 1/2,030 mol/g; available from Dow Corning Toray Co., Ltd.) as a reactive functional group-containing organopolysiloxane and 8 g of N-acetyl-DL-homocysteine thiolactone. The contents of the flask were heated to 100° C. and stirred for 3 h in a nitrogen atmosphere, thereby synthesizing a sulfanyl group-containing radical-reactive organopolysiloxane A. As a result of subjecting the resulting reaction solution to potentiometric titration measurement to determine a residual amount of an amino group remaining in the reaction solution, it was confirmed that 99% of the amino group of the side-chain primary aminopropyl-modified organopolysiloxane as the raw material was reacted with N-acetyl-DL-homocysteine thiolactone (conversion rate of amino group: 99%). Therefore, the number of moles of the sulfanyl group per a unit mass of the radical-reactive organopolysiloxane A was 1/2,210 mol/g. As a result of subjecting the radical-reactive organopolysiloxane A to GPC measurement, it was confirmed that the radical-reactive organopolysiloxane A had a weight-average molecular weight of 30,000.

Synthesis Examples 2 to 4

The procedure of Synthesis Example 2 was carried out in the same manner as in Synthesis Example 1, and the procedures of Synthesis Examples 3 and 4 were carried out in the same manner as in Synthesis Example 1 except that the number of moles of an amino group per a unit mass of the side-chain primary aminopropyl-modified organopolysiloxane and the weight-average molecular weight thereof were changed as shown in Table 1, thereby obtaining radical-reactive organopolysiloxanes B to D. Meanwhile, as the side-chain primary aminopropyl-modified organopolysiloxane, "AMS-162" (available from Gelest Inc.) was used in Synthesis Example 3, and "KF-8003" (available from Shin-Etsu Chemical Co., Ltd.) was used in Synthesis Example 4.

TABLE 1

| | | Synthesis Examples | | | |
|---|---|---|---|---|---|
| | | 1 | 2 | 3 | 4 |
| Side-chain primary aminopropyl-modified organopoly-siloxane | Weight-average molecular weight | 30,000 | 30,000 | 10,000 | 50,000 |
| | Number of moles of amino group [1] (mol/g) | 1/2,030 | 1/2,060 | 1/1,000 | 1/1,970 |
| Conversion rate of amino group by reaction (%) | | 99 | 98 | 97 | 98 |
| Radical-reactive organopoly-siloxane | Name | A | B | C | D |
| | Weight-average molecular weight | 30,000 | 30,000 | 10,000 | 50,000 |
| | Number of moles of sulfanyl group [2] (mol/g) | 1/2,210 | 1/2,260 | 1/1,200 | 1/2,170 |

Note
[1] Per a unit mass of the side-chain primary organopolysiloxane
[2] Per a unit mass of the radical-reactive organopolysiloxane

Example 1

<Synthesis of Organopolysiloxane Graft Polymer E>

A separable flask equipped with a reflux condenser, a thermometer, a nitrogen inlet tube and a stirrer was charged with 101.0 g of ethanol. While stirring the ethanol under reflux at 80° C. in a nitrogen atmosphere, the following solutions (a) and (b) were respectively charged in separate dropping funnels and added dropwise at the same time to the flask over 1 h.

Solution (a): Solution prepared by mixing 76.8 g of DMAAm, 19.2 g of N-tert-butyl acrylamide (hereinafter referred to as "t-BuAAm") and 96.0 g of ethanol.

Solution (b): Solution prepared by mixing 64.0 g of the radical-reactive organopolysiloxane A synthesized in the above Synthesis Example 1, 0.03 g of 2,2'-azobis(2,4-dimethyl valeronitrile) "V-65B" (available from Wako Pure Chemical Industries, Ltd.; azo-based polymerization initiator) and 43.0 g of ethanol.

After completion of the dropwise addition, the reaction mixture was stirred at 80° C. for 3 h, and then cooled. The obtained reaction time was 4 h in total. The reaction mixture was allowed to stand at room temperature (25° C.) under reduced pressure (20 kPa) over 4 h to remove ethanol therefrom, thereby obtaining a mixture containing an organopolysiloxane graft polymer E as a white solid. As a result of measuring a sulfanyl group residual rate of the resulting product by the above method, it was confirmed that the sulfanyl group residual rate was 3%.

The content of the unsaturated monomer-derived polymer that was unbonded to the organopolysiloxane graft polymer in the mixture containing the organopolysiloxane graft polymer E obtained after completion of the reaction was measured by the above method. As a result, it was confirmed that the content of the unbonded polymer in the mixture was 29% by mass. The mass ratio (a/b) of the organopolysiloxane segment (a) to the unsaturated monomer-derived polymer segment (b) in the organopolysiloxane graft polymer E was calculated from the above formula (I). As a result, it was confirmed that the mass ratio (a/b) was 56/44.

The resulting mixture containing the organopolysiloxane graft polymer E was purified by silica gel column chromatography (eluent: methanol/chloroform=15/85 (v/v)), thereby obtaining the organopolysiloxane graft polymer E as a white solid. The thus isolated organopolysiloxane graft polymer E was subjected to the above nuclear magnetic resonance ($^1$H-NMR) analysis to determine a mass ratio (a/b) of the organopolysiloxane graft polymer E. As a result, it was confirmed that the mass ratio (a/b) was 56/44 and therefore was identical to the above calculation result. As a result of subjecting the isolated organopolysiloxane graft polymer E to GPC measurement, it was confirmed that the weight-average molecular weight thereof was 63,000.

The mixture containing the above obtained organopolysiloxane graft polymer E and the purified organopolysiloxane graft polymer E were subjected to evaluation of a hair setting property thereof. The results are shown in Table 2. The results of evaluation for the setting property were substantially unchanged between before and after the purification treatment, and therefore it is considered that the influence of the unsaturated monomer-derived polymer that is unbonded to the organopolysiloxane on a hair setting property of the hair cosmetic can be ignored. In addition, the hair setting property of the hair cosmetic according to the present invention is largely influenced by a room temperature elastic modulus and a high-temperature elastic modulus of the polymer. Therefore, from the results shown in Table 2, it is suggested that the influence of the unsaturated monomer-derived polymer that is unbonded to the organopolysiloxane on the room temperature elastic modulus and the high-temperature elastic modulus is also low. For this reason, in the subsequent Examples, etc., the mixture containing the organopolysiloxane graft polymer which was subjected to no isolation treatment was used for the evaluation.

TABLE 2

|  | Mixture containing organopolysiloxane graft polymer E | Organopolysiloxane graft polymer E |
| --- | --- | --- |
| Finish of hair style | 4.8 | 4.8 |
| Touch feeling (less stickiness) | 4.6 | 4.8 |
| Retentivity of hair style after setting | 4.8 | 4.8 |

Example 2

<Synthesis of Organopolysiloxane Graft Polymer F>

A separable flask equipped with a reflux condenser, a thermometer, a nitrogen inlet tube and a stirrer was charged with 100.0 g of ethanol. While stirring the ethanol under reflux at 80° C. in a nitrogen atmosphere, the following solution (a) was charged in a dropping funnel and added dropwise to the flask over 2 h.

Solution (a): Solution prepared by mixing 50.0 g of DMAAm, 50.0 g of the radical-reactive organopolysiloxane C (synthesized in the above Synthesis Example 3), 0.1 g of "V-65B" used in Example 1 and 400.0 g of ethanol.

After completion of the dropwise addition, the obtained reaction mixture was stirred at 80° C. under reflux for 4 h, and then cooled. The reaction time was 6 h in total. The reaction mixture was allowed to stand at room temperature (25° C.) under reduced pressure (20 kPa) over 4 h to remove the solvent therefrom, thereby obtaining a mixture containing an organopolysiloxane graft polymer F as a light-yellow solid. As a result of measuring a sulfanyl group residual rate of the resulting product by the above method, it was confirmed that the sulfanyl group residual rate was 2%.

The composition of the unsaturated monomer-derived polymer that was unbonded to the organopolysiloxane graft polymer in the mixture containing the organopolysiloxane graft polymer F obtained after completion of the reaction was measured by the above method. As a result, it was confirmed that the content of the unbonded polymer in the mixture was 17% by mass. The mass ratio (a/b) of the organopolysiloxane segment (a) to the unsaturated monomer-derived polymer segment (b) in the organopolysiloxane graft polymer F was calculated from the above formula (I). As a result, it was confirmed that the mass ratio (a/b) was 60/40. The weight-average molecular weight (MWtcalc) of the organopolysiloxane graft polymer F as calculated from the above formula (II) was 17,000.

Example 3

<Synthesis of Organopolysiloxane Graft Polymer G>

A separable flask equipped with a reflux condenser, a thermometer, a nitrogen inlet tube and a stirrer was charged with 40.0 g of tetrahydrofuran. While stirring the tetrahydrofuran under reflux at 70° C. in a nitrogen atmosphere, the following solution (a) was charged in a dropping funnel and added dropwise to the flask over 2 h.

Solution (a): Solution prepared by mixing 28.0 g of DMAAm, 28.0 g of tBuAAm, 24.0 g of a side-chain mercapto-modified organopolysiloxane "KF-2001" (available from Shin-Etsu Chemical Co., Ltd.; weight-average molecular weight: 16,000; number of moles of a sulfanyl group: 1/1,900 mol/g), 0.08 g of "V-65B" used in Example 1 and 360.0 g of tetrahydrofuran.

After completion of the dropwise addition, the obtained reaction mixture was stirred at 70° C. under reflux for 4 h, and then cooled. The reaction time was 6 h in total. The reaction mixture was allowed to stand at room temperature (25° C.) under reduced pressure (20 kPa) over 4 h to remove the solvent therefrom, thereby obtaining a mixture containing an organopolysiloxane graft polymer G as a white solid. As a result of measuring a sulfanyl group residual rate of the resulting product by the above method, it was confirmed that the sulfanyl group residual rate was 2%.

The content of the unsaturated monomer-derived polymer that was unbonded to the organopolysiloxane graft polymer in the mixture containing the organopolysiloxane graft polymer G obtained after completion of the reaction was measured by the above method. As a result, it was confirmed that the content of the unbonded polymer in the mixture was 26% by mass. The mass ratio (a/b) of the organopolysiloxane segment (a) to the unsaturated monomer-derived polymer segment (b) in the organopolysiloxane graft polymer G was calculated from the above formula (I). As a result, it was confirmed that the mass ratio (a/b) was 54/46.

Example 4

<Synthesis of Organopolysiloxane Graft Polymer H>

A separable flask equipped with a reflux condenser, a thermometer, a nitrogen inlet tube and a stirrer was charged with 100.0 g of ethyl acetate. While stirring the ethyl acetate under reflux at 80° C. in a nitrogen atmosphere, the following solution (a) was charged in a dropping funnel and added dropwise to the flask over 2 h.

Solution (a): Solution prepared by mixing 60.0 g of DMAAm, 40.0 g of "KF-2001" used in Example 3, 0.1 g of "V-65B" used in Example 1 and 400.0 g of ethyl acetate.

After completion of the dropwise addition, the obtained reaction mixture was stirred at 80° C. under reflux for 4 h, and then cooled. The reaction time was 6 h in total. The reaction mixture was allowed to stand at room temperature (25° C.) under reduced pressure (20 kPa) over 4 h to remove the solvent therefrom, thereby obtaining a mixture containing an organopolysiloxane graft polymer H as a light-yellow solid. As a result of measuring a sulfanyl group residual rate of the resulting product by the above method, it was confirmed that the sulfanyl group residual rate was 0%.

The content of the unsaturated monomer-derived polymer that was unbonded to the organopolysiloxane graft polymer in the mixture containing the organopolysiloxane graft polymer H obtained after completion of the reaction was measured by the above method. As a result, it was confirmed that the content of the unbonded polymer in the mixture was 0% by mass. The mass ratio (a/b) of the organopolysiloxane segment (a) to the unsaturated monomer-derived polymer segment (b) in the organopolysiloxane graft polymer H was calculated from the above formula (I). As a result, it was confirmed that the mass ratio (a/b) was 40/60. In addition, as a result of subjecting the organopolysiloxane graft polymer H to GPC measurement, it was confirmed that the weight-average molecular weight (MWt) of the organopolysiloxane graft polymer H was 36,000.

Example 5

<Synthesis of Organopolysiloxane Graft Polymer I>

A separable flask equipped with a reflux condenser, a thermometer, a nitrogen inlet tube and a stirrer was charged with 60.0 g of ethanol. While stirring the ethanol at 65° C. in a nitrogen atmosphere, the following solutions (a) and (b) were respectively charged in separate dropping funnels and added dropwise at the same time to the flask over 1 h.

Solution (a): Solution prepared by mixing 33.6 g of DMAAm, 8.4 g of t-BuAAm and 54.0 g of ethanol.

Solution (b): Solution prepared by mixing 18.0 g of the radical-reactive organopolysiloxane A (synthesized in the above Synthesis Example 1), 0.1 g of "V-65B" used in Example 1 and 36.0 g of ethanol.

After completion of the dropwise addition, the obtained reaction mixture was stirred at 65° C. for 5 h, and then cooled. The reaction time was 6 h in total. The reaction mixture was allowed to stand at room temperature (25° C.) under reduced pressure (20 kPa) over 4 h to remove the solvent therefrom, thereby obtaining a mixture containing an organopolysiloxane graft polymer I as a white solid. As a result of measuring a sulfanyl group residual rate of the resulting product by the above method, it was confirmed that the sulfanyl group residual rate was 0%.

The content of the unsaturated monomer-derived polymer that was unbonded to the organopolysiloxane graft polymer in the mixture containing the organopolysiloxane graft polymer I obtained after completion of the reaction was measured by the above method. As a result, it was confirmed that the content of the unbonded polymer in the mixture was 47% by mass. The mass ratio (a/b) of the organopolysiloxane segment (a) to the unsaturated monomer-derived polymer segment (b) in the organopolysiloxane graft polymer I was calculated from the above formula (I). As a result, it was confirmed that the mass ratio (a/b) was 57/43.

Examples 6, 9 and 10

<Synthesis of Organopolysiloxane Graft Polymers J, M and N>

The same procedure as in Example 5 was repeated except that in Example 5, the amounts of the radical-reactive organopolysiloxane A obtained in Synthesis Example 1, DMAAm and tBuAAm added were varied as shown in Table 3, thereby obtaining a mixture containing an organopolysiloxane graft polymer J, M or N. The results are shown in Table 3.

The resulting mixture containing the organopolysiloxane graft polymer N was purified by silica gel column chromatography (eluent: methanol/chloroform=15/85 (v/v)), thereby obtaining the organopolysiloxane graft polymer N as a white solid. The thus isolated organopolysiloxane graft polymer N was subjected to the above nuclear magnetic resonance ($^1$H-NMR) analysis to determine a mass ratio (a/b) of the organopolysiloxane segment (a) to the unsaturated monomer-derived polymer segment (b) in the organopolysiloxane graft polymer. As a result, it was confirmed that the mass ratio (a/b) was 64/36 and therefore was almost identical to the result (65/35) calculated from the formula (I).

TABLE 3

|  | Examples | | |
| --- | --- | --- | --- |
|  | 6 | 9 | 10 |
| Organopolysiloxane graft polymer | J | M | N |
| Radical-reactive organopolysiloxane A (g) | 24.0 | 24.0 | 30.0 |
| DMAAm (g) | 25.2 | 36.0 | 24.0 |
| tBuAAm (g) | 10.8 | 0.0 | 6.0 |
| Sulfanyl group residual rate (%) | 3 | 3 | 17 |
| Mass ratio (a/b) | 58/42 | 44/56 | 65/35 |

Example 7

<Synthesis of Organopolysiloxane Graft Polymer K>

A separable flask equipped with a reflux condenser, a thermometer, a nitrogen inlet tube and a stirrer was charged with 50.0 g of ethanol. While stirring the ethanol at 65° C. in a nitrogen atmosphere, the following solutions (a) and (b) were respectively charged in separate dropping funnels and added dropwise at the same time to the flask over 1 h.

Solution (a): Solution prepared by mixing 28.8 g of DMAAm, 7.2 g of methyl methacrylate (hereinafter referred to as "MMA") and 54.0 g of ethanol. Solution (b): Solution prepared by mixing 24.0 g of the radical-reactive organopolysiloxane B (synthesized in the above Synthesis Example 2), 0.1 g of "V-65B" used in Example 1 and 36.0 g of ethanol.

After completion of the dropwise addition, the obtained reaction mixture was stirred at 65° C. for 6 h, and then cooled. The reaction time was 7 h in total. The reaction mixture was allowed to stand at room temperature (25° C.) under reduced pressure (20 kPa) over 4 h to remove the solvent therefrom, thereby obtaining a mixture containing an organopolysiloxane graft polymer K as a light-yellow solid. As a result of measuring a sulfanyl group residual rate of the resulting product by the above method, it was confirmed that the sulfanyl group residual rate was 0%.

The content of the unsaturated monomer-derived polymer that was unbonded to the organopolysiloxane graft polymer in the mixture containing the organopolysiloxane graft polymer K obtained after completion of the reaction was measured by the above method. As a result, it was confirmed that the content of the unbonded polymer in the mixture was 8% by mass. The mass ratio (a/b) of the organopolysiloxane segment (a) to the unsaturated monomer-derived polymer segment (b) in the organopolysiloxane graft polymer K was calculated from the above formula (I). As a result, it was confirmed that the mass ratio (a/b) was 43/57.

Example 8

<Synthesis of Organopolysiloxane Graft Polymer L>

The same procedure as in Example 7 was repeated except that MMA was replaced with N,N-dimethylaminopropyl acrylamide (hereinafter referred to as "DMAPAA"), thereby obtaining a mixture containing an organopolysiloxane graft polymer L as a yellow solid. As a result of measuring a sulfanyl group residual rate of the resulting product by the above method, it was confirmed that the sulfanyl group residual rate was 5%.

Example 11

<Synthesis of Organopolysiloxane Graft Polymer O>

A separable flask equipped with a reflux condenser, a thermometer, a nitrogen inlet tube and a stirrer was charged with 50.0 g of ethanol. While stirring the ethanol at 65° C. in a nitrogen atmosphere, the following solutions (a) and (b) were respectively charged in separate dropping funnels and added dropwise at the same time to the flask over 1 h.

Solution (a): Solution prepared by mixing 28.8 g of DMAAm, 7.2 g of tBuAAm and 54.0 g of ethanol.

Solution (b): Solution prepared by mixing 24.0 g of the radical-reactive organopolysiloxane D (synthesized in the above Synthesis Example 4), 0.1 g of "V-65B" used in Example 1 and 36.0 g of ethanol.

After completion of the dropwise addition, the obtained reaction mixture was stirred at 65° C. for 5 h, and then cooled. The reaction time was 6 h in total. The reaction mixture was allowed to stand at room temperature (25° C.) under reduced pressure (20 kPa) over 4 h to remove the solvent therefrom, thereby obtaining a mixture containing an organopolysiloxane graft polymer O as a light-yellow solid. As a result of measuring a sulfanyl group residual rate of the resulting product by the above method, it was confirmed that the sulfanyl group residual rate was 2%.

The content of the unsaturated monomer-derived polymer that was unbonded to the organopolysiloxane graft polymer in the mixture containing the organopolysiloxane graft polymer O obtained after completion of the reaction was measured by the above method. As a result, it was confirmed that the content of the unbonded polymer in the mixture was 26% by mass. The mass ratio (a/b) of the organopolysiloxane segment (a) to the unsaturated monomer-derived polymer segment (b) in the organopolysiloxane graft polymer O was calculated from the above formula (I). As a result, it was confirmed that the mass ratio (a/b) was 54/46.

The water dispersibility of the respective organopolysiloxane graft polymers obtained in Examples 1 to 11 and the elastic modulus of a film formed from the respective organopolysiloxane graft polymer mixtures were measured. The results are shown in Table 4.

TABLE 4

| | Examples | | | | | |
|---|---|---|---|---|---|---|
| | 1 | 2 | 3 | 4 | 5 | 6 |
| Organopolysiloxane graft polymer | E | F | G | H | I | J |
| Main chain | | | | | | |
| Weight-average molecular weight | 30,000 | 10,000 | 16,000 | 16,000 | 30,000 | 30,000 |
| Content of main chain segment in organopolysiloxane graft polymer (% by mass) | 56 | 60 | 54 | 40 | 57 | 58 |
| Side chain | | | | | | |
| Composition of DMAAm (% by mass)[1] | 80 | 100 | 50 | 100 | 80 | 70 |
| Comonomer | tBuAAm | — | tBuAAm | — | tBuAAm | tBuAAm |
| Polymerization solvent | Ethanol | Ethanol | THF | Ethyl acetate | Ethanol | Ethanol |
| Molecular weight between graft points | 2,270 | 1,230 | 1,940 | 1,910 | 2,210 | 2,290 |
| Weight-average molecular weight | 63,000[2] | 17,000[3] | 30,000[3] | 36,000[2] | 53,000[3] | 52,000[3] |
| Water dispersibility (transmittance of 2.5% by mass solution (%)) | 99 | 100 | 80 | 97 | 99 | 98 |
| Elastic modulus at room temperature (25° C.) (Pa) | $9.96 \times 10^6$ | $1.59 \times 10^7$ | $5.09 \times 10^6$ | $3.38 \times 10^6$ | $8.78 \times 10^6$ | $7.03 \times 10^6$ |
| Elastic modulus at high temperature (150° C.) (Pa) | $5.45 \times 10^4$ | $1.38 \times 10^5$ | $2.34 \times 10^3$ | $1.93 \times 10^4$ | $6.38 \times 10^5$ | $1.98 \times 10^5$ |

| | Examples | | | | |
|---|---|---|---|---|---|
| | 7 | 8 | 9 | 10 | 11 |
| Organopolysiloxane graft polymer | K | L | M | N | O |
| Main chain | | | | | |
| Weight-average molecular weight | 30,000 | 30,000 | 30,000 | 30,000 | 50,000 |
| Content of main chain segment in organopolysiloxane graft polymer (% by mass) | 43 | — | 44 | 65 | 54 |
| Side chain | | | | | |
| Composition of DMAAm (% by mass)[1] | 80 | 80 | 100 | 80 | 80 |
| Comonomer | MMA | DMAPAA | — | tBuAAm | tBuAAm |
| Polymerization solvent | Ethanol | Ethanol | Ethanol | Ethanol | Ethanol |
| Molecular weight between graft points | 2,170 | 2,280 | 2,670 | 2,260 | 2,210 |
| Weight-average molecular weight | 68,000[3] | —[4] | 68,000[3] | 46,000[3] | 93,000[3] |
| Water dispersibility (transmittance of 2.5% by mass solution (%)) | 98 | 98 | 100 | 99 | 95 |
| Elastic modulus at room temperature (25° C.) (Pa) | $7.73 \times 10^6$ | $7.05 \times 10^6$ | $6.64 \times 10^6$ | $5.02 \times 10^6$ | $1.29 \times 10^7$ |
| Elastic modulus at high temperature (150° C.) (Pa) | $1.89 \times 10^5$ | $9.42 \times 10^4$ | $6.93 \times 10^4$ | $7.17 \times 10^3$ | $4.88 \times 10^4$ |

Note
[1] In an unsaturated monomer-derived polymer segment;
[2] MWt;
[3] MWtcalc;
[4] Because the mass ratio (a/b) was unmeasured.
DMAAm: N,N-dimethyl acrylamide;
tBuAAm: N-tert-butyl acrylamide;
MMA: methyl methacrylate;
DMAPAA: N,N-dimethylaminopropyl acrylamide;
EMA: ethyl methacrylate

Comparative Example 1

<Synthesis of Organopolysiloxane Graft Polymer P>

A separable flask equipped with a reflux condenser, a thermometer, a nitrogen inlet tube and a stirrer was charged with 50.0 g of ethanol. While stirring the ethanol at 65° C. in a nitrogen atmosphere, the following solutions (a) and (b) were respectively charged in separate dropping funnels and added dropwise at the same time to the flask over 1 h.

Solution (a): Solution prepared by mixing 14.4 g of DMAAm, 21.6 g of tBuAAm and 60.0 g of ethanol.

Solution (b): Solution prepared by mixing 24.0 g of the radical-reactive organopolysiloxane B (synthesized in the above Synthesis Example 2), 0.1 g of "V-65B" used in Example 1 and 36.0 g of ethanol.

After completion of the dropwise addition, the obtained reaction mixture was stirred at 65° C. for 5 h, and then cooled. The reaction mixture was allowed to stand at room temperature under reduced pressure (20 kPa) over 4 h to remove the solvent therefrom, thereby obtaining a mixture containing an organopolysiloxane graft polymer P as a light-yellow solid.

Comparative Example 2

<Synthesis of Organopolysiloxane Graft Polymer Q>

A separable flask equipped with a reflux condenser, a thermometer, a nitrogen inlet tube and a stirrer was charged with 61.3 g of ethanol. While stirring the ethanol at 80° C. under reflux in a nitrogen atmosphere, the following solutions (a) and (b) were respectively charged in separate dropping funnels and added dropwise at the same time to the flask over 1 h.

Solution (a): Solution prepared by mixing 12.8 g of DMAAm, 3.2 g of tBuAAm and 16.0 g of ethanol.

Solution (b): Solution prepared by mixing 64.0 g of the radical-reactive organopolysiloxane B synthesized in the above Synthesis Example 2, 0.03 g of 2,2'-azobis(2,4-dimethyl valeronitrile) "V-65B" (available from Wako Pure Chemical Industries, Ltd.; azo-based polymerization initiator) and 43.0 g of ethanol.

After completion of the dropwise addition, the obtained reaction mixture was stirred at 80° C. for 3 h, and then cooled. The reaction time was 4 h in total. The reaction mixture was allowed to stand at room temperature (25° C.) under reduced pressure (20 kPa) over 4 h to remove the ethanol therefrom, thereby obtaining a mixture containing an organopolysiloxane graft polymer Q as a white solid. As a result of calculating the content of the organopolysiloxane segment in the resulting organopolysiloxane graft polymer from the amounts of the raw materials used in the above reaction, it was confirmed that the organopolysiloxane segment content was 80% or more.

Comparative Example 3

<Synthesis of Organopolysiloxane Graft Polymer R>

A separable flask equipped with a reflux condenser, a thermometer, a nitrogen inlet tube and a stirrer was charged with 75.0 g of ethanol. While stirring the ethanol at 65° C. in a nitrogen atmosphere, the following solutions (a) and (b) were respectively charged in separate dropping funnels and added dropwise at the same time to the flask over 1 h.

Solution (a): Solution prepared by mixing 45.0 g of DMAPAA and 135.0 g of ethanol.

Solution (b): Solution prepared by mixing 30.0 g of the radical-reactive organopolysiloxane D (synthesized in the above Synthesis Example 4), 0.4 g of "V-65B" used in Example 1 and 90.0 g of ethanol.

After completion of the dropwise addition, the obtained reaction mixture was stirred at 65° C. for 5 h, and then cooled, thereby obtaining an ethanol solution of a mixture containing an organopolysiloxane graft polymer R.

Comparative Example 4

<Synthesis of Organopolysiloxane Graft Polymer S>

The same procedure as in Comparative Example 3 was repeated except that DMAPAA in the solution (a) was replaced with ethyl methacrylate (hereinafter referred to as "EMA"), thereby obtaining an ethanol solution of a mixture containing an organopolysiloxane graft polymer S.

The water dispersibility of the respective organopolysiloxane graft polymers obtained in Comparative Examples 1 to 4 and the elastic modulus of a film formed from the respective organopolysiloxane graft polymer mixtures were measured. The results are shown in Table 5.

TABLE 5

| | Comparative Examples | | | |
|---|---|---|---|---|
| | 1 | 2 | 3 | 4 |
| Organopolysiloxane graft polymer Main chain | P | Q | R | S |
| Weight-average molecular weight Side chain | 30,000 | 30,000 | 50,000 | 50,000 |
| Composition of DMAAm (% by mass) | 40 | 80 | 0 | 0 |
| Comonomer | tBuAAm | tBuAAm | DMAPAA | EMA |
| Polymerization solvent | Ethanol | Ethanol | Ethanol | Ethanol |
| Water dispersibility (transmittance of 2.5% by mass solution (%)) | —(*) | —(*) | 97 | —(*) |
| Elastic modulus at room temperature (25° C.) (Pa) | —(**) | $2.55 \times 10^6$ | $4.31 \times 10^4$ | $4.98 \times 10^6$ |
| Elastic modulus at high temperature (150° C.) (Pa) | —(**) | $<1.00 \times 10^1$ | $<1.00 \times 10^1$ | $3.83 \times 10^4$ |

Note
(*)Unmeasurable owing to production of precipitates.
(**)Unmeasurable owing to difficulty in forming a film used for measuring the elastic modulus.

The organopolysiloxane graft polymers obtained in the respective Examples and Comparative Examples were subjected to evaluation of hair setting property according to the above evaluation method. The results are collectively shown in Table 6.

Meanwhile, the organopolysiloxane graft polymers P, Q and S obtained in Comparative Examples 1, 2 and 4, respectively, were unmeasurable for a water dispersibility thereof because they suffered from formation of precipitates upon the measurement of the water dispersibility. Since a hair setting agent is usually used in the form of a spraying agent, if the hair cosmetic suffers from formation of any precipitates, there tends to arise problems such as clogging. Therefore, in fact, it may be difficult to use the thus precipitated hair cosmetic in the form of a spraying agent. Thus, the organopolysiloxane graft polymers P, Q and S were not evaluated for their hair setting property.

TABLE 6

|  | Examples | | | | | | | | | | | Comparative Examples | | | |
| --- | --- | --- | --- | --- | --- | --- | --- | --- | --- | --- | --- | --- | --- | --- | --- |
|  | 1 | 2 | 3 | 4 | 5 | 6 | 7 | 8 | 9 | 10 | 11 | 1 | 2 | 3 | 4 |
| Organopolysiloxane graft polymer | E | F | G | H | I | J | K | L | M | N | O | P | Q | R | S |
| Finish of hair style | 4.8 | 4.0 | 4.6 | 5.0 | 5.0 | 4.6 | 4.0 | 4.6 | 4.8 | 4.6 | 4.8 | — | — | 3.0 | — |
| Touch feeling (less stickiness) | 4.6 | 4.0 | 4.4 | 4.6 | 4.2 | 4.0 | 3.6 | 4.8 | 4.0 | 4.6 | 4.4 | — | — | 1.4 | — |
| Hair style retentivity after setting | 4.8 | 4.4 | 4.8 | 5.0 | 5.0 | 4.8 | 3.2 | 4.8 | 4.6 | 4.6 | 4.8 | — | — | 1.2 | — |

As apparently recognized from the results shown in Tables 4 to 6, it was confirmed that the organopolysiloxane graft polymers according to the present invention could exhibit a high elastic modulus at room temperature, a thermoplasticity as a property capable of being softened upon heating, a high dispersibility in water. Further, the hair cosmetics using the respective organopolysiloxane graft polymers according to the present invention suffered from less stickiness upon or after hair setting, and were excellent in hair setting property and hair style retentivity after the setting.

INDUSTRIAL APPLICABILITY

The organopolysiloxane graft polymer according to the present invention can exhibit a good touch feeling without stickiness and can be well uniformly dispersed in water, and therefore can be suitably used as a hair cosmetic capable of firmly fixing a hair style and maintaining the hair style for a long period of time.

The invention claimed is:

1. A method for treating hair, comprising applying an organopolysiloxane graft polymer onto the hair,
the organopolysiloxane graft polymer comprising an organopolysiloxane segment as a main chain thereof and an unsaturated monomer-derived polymer segment as a side chain thereof, in which the unsaturated monomer-derived polymer segment contains a repeating unit derived from N,N-dimethyl acrylamide in an amount of not less than 50% by mass and not more than 100% by mass, and a content of the organopolysiloxane segment in the organopolysiloxane graft polymer is not less than 10% by mass and not more than 70% by mass,
wherein the elastic modulus of the organopolysiloxane graft polymer at 25° C. is between $3.38 \times 10^6$ Pa and $1.59 \times 10^7$ Pa, the elastic modulus of the organopolysiloxane graft polymer at 150° C. is between $2.34 \times 10^3$ Pa and $6.38 \times 10^5$ Pa, and the water dispersibility of the organopolysiloxane graft polymer allows at least 70% transmittance.

2. The method for treating hair according to claim 1, wherein the organopolysiloxane segment has a weight-average molecular weight of not less than 3,000 and not more than 200,000.

3. The method for treating hair according to claim 1, wherein among the organopolysiloxane segments, the organopolysiloxane segment being present between the adjacent unsaturated monomer-derived polymer segments has a number-average molecular weight (MNg) of not less than 500 and not more than 10,000.

4. The method for treating hair according to claim 1, wherein the unsaturated monomer-derived polymer segment further comprises a repeating unit derived from at least one unsaturated monomer selected from the group consisting of (meth)acrylamides except for N,N-dimethyl acrylamide, and (meth)acrylates.

5. The method for treating hair according to claim 4, wherein the (meth)acrylamides is at least one (meth)acrylamide selected from the group consisting of acrylamide, methacrylamide, N,N-diethyl (meth)acrylamide, N-isopropyl (meth)acrylamide, N-tert-butyl (meth)acrylamide, N-cyclohexyl (meth)acrylamide, N-tert-octyl (meth)acrylamide, diacetone (meth)acrylamide, N,N-dimethylaminopropyl (meth)acrylamide, N-methylol (meth)acrylamide and N-hydroxyethyl (meth)acrylamide.

6. The method for treating hair according to claim 4, wherein the (meth)acrylates is at least one (meth)acrylate selected from the group consisting of methyl (meth)acrylate, ethyl (meth)acrylate, propyl (meth)acrylate, isobutyl (meth)acrylate, n-butyl (meth)acrylate, tert-butyl (meth)acrylate, hexyl (meth)acrylate, octyl (meth)acrylate, 2-ethylhexyl (meth)acrylate, decyl (meth)acrylate, dodecyl (meth)acrylate, cyclohexyl (meth)acrylate, 2-hydroxyethyl (meth)acrylate, polyethylene glycol (meth)acrylate, and polyethylene glycol monomethyl ether (meth)acrylate.

7. The method for treating hair according to claim 1, wherein a mass ratio (a/b) of the organopolysiloxane segment (a) to the unsaturated monomer-derived polymer segment (b) is not less than 10/90 and not more than 70/30.

8. The method for treating hair according to claim 1, wherein a weight-average molecular weight of the organopolysiloxane graft polymer is not less than 10,000 and not more than 200,000.

9. The method for treating hair according to claim 1, further comprising straightening the hair with a straightening iron.

* * * * *